(12) United States Patent
Sogard et al.

(10) Patent No.: US 9,415,567 B2
(45) Date of Patent: Aug. 16, 2016

(54) SYNTHETIC COMPOSITE STRUCTURES

(75) Inventors: David J. Sogard, Edina, MN (US);
Jason P. Hill, Brooklyn Park, MN (US);
Scott Smith, Chaska, MN (US); Patrick A. Haverkost, Brooklyn Center, MN (US); Susan A. Shoemaker, Elk River, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 2264 days.

(21) Appl. No.: 12/348,711

(22) Filed: Jan. 5, 2009

(65) Prior Publication Data

US 2009/0117334 A1 May 7, 2009

Related U.S. Application Data

(63) Continuation-in-part of application No. 12/012,919, filed on Feb. 5, 2008.

(60) Provisional application No. 60/899,445, filed on Feb. 5, 2007.

(51) Int. Cl.
*B32B 15/00* (2006.01)
*A61F 2/24* (2006.01)
(Continued)

(52) U.S. Cl.
CPC ............... *B32B 15/00* (2013.01); *A61F 2/2412* (2013.01); *A61F 2/2418* (2013.01); *B32B 3/14* (2013.01); *B32B 3/266* (2013.01); *B32B 7/12* (2013.01); *B32B 9/02* (2013.01); *B32B 15/04* (2013.01); *B32B 15/08* (2013.01); *B32B 15/18* (2013.01); *B32B 27/16* (2013.01); *B32B 27/281* (2013.01); *B32B 27/283* (2013.01); *B32B 27/302* (2013.01); *B32B 27/304* (2013.01); *B32B 27/32* (2013.01); *B32B 27/36* (2013.01); *B32B 27/365* (2013.01); *B32B 27/40* (2013.01); *A61F 2220/005* (2013.01); *A61F 2220/0041* (2013.01); *A61F 2220/0058* (2013.01); *A61F 2220/0066* (2013.01); *B32B 2250/44* (2013.01); *B32B 2307/50* (2013.01); *B32B 2307/51* (2013.01); *B32B 2307/514* (2013.01); *B32B 2307/542* (2013.01); *B32B 2307/546* (2013.01);
(Continued)

(58) Field of Classification Search
USPC ....................................................... 623/1.26
See application file for complete search history.

(56) References Cited

U.S. PATENT DOCUMENTS

2004/0117004 A1* 6/2004 Osborne et al. ............... 623/1.36
2004/0243222 A1* 12/2004 Osborne et al. ............... 623/1.24
(Continued)

FOREIGN PATENT DOCUMENTS

WO 99/01245 1/1999

OTHER PUBLICATIONS

International Search Report from Parent Application. Aug. 7, 2008. 3 pgs.
(Continued)

*Primary Examiner* — Nathan Van Sell
(74) *Attorney, Agent, or Firm* — Pauly, DeVries Smith & Deffner, L.L.C.

(57) ABSTRACT

A composite biomaterial having a continuous metal sheet with arcuate members that define a first fenestration pattern, and a polymer layer over at least one surface of the continuous metal sheet. The arcuate members elastically stretch to allow the continuous metal sheet to bend in more than one axis without buckling or wrinkling.

5 Claims, 14 Drawing Sheets

(51) Int. Cl.
- B32B 7/12 (2006.01)
- B32B 9/02 (2006.01)
- B32B 15/04 (2006.01)
- B32B 15/08 (2006.01)
- B32B 15/18 (2006.01)
- B32B 27/16 (2006.01)
- B32B 27/28 (2006.01)
- B32B 27/30 (2006.01)
- B32B 27/32 (2006.01)
- B32B 27/36 (2006.01)
- B32B 27/40 (2006.01)
- B32B 3/14 (2006.01)
- B32B 3/26 (2006.01)

(52) U.S. Cl.
CPC ....... *B32B2307/554* (2013.01); *B32B 2535/00* (2013.01); *B32B 2605/08* (2013.01); *B32B 2605/18* (2013.01); *Y10T 29/49826* (2015.01); *Y10T 428/24273* (2015.01); *Y10T 428/24479* (2015.01)

(56) References Cited

U.S. PATENT DOCUMENTS

| | | | |
|---|---|---|---|
| 2005/0137681 A1* | 6/2005 | Shoemaker et al. | 623/1.23 |
| 2005/0267560 A1* | 12/2005 | Bates | 623/1.1 |
| 2006/0074483 A1* | 4/2006 | Schrayer | 623/2.1 |

OTHER PUBLICATIONS

An International Search Report for related PCT Application No. PCT/US2009/006746 dated Mar. 31, 2010. 11 pgs.

* cited by examiner

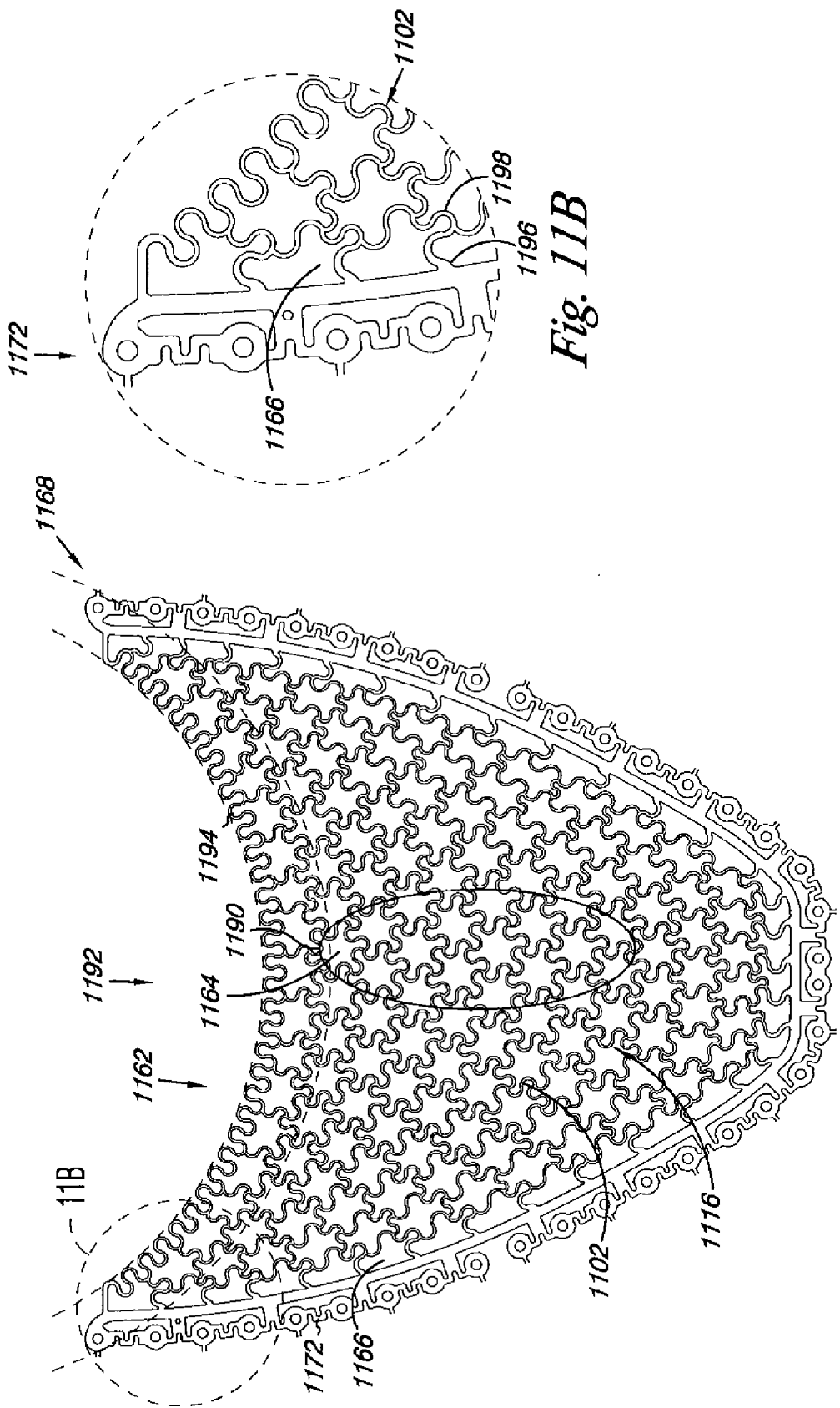

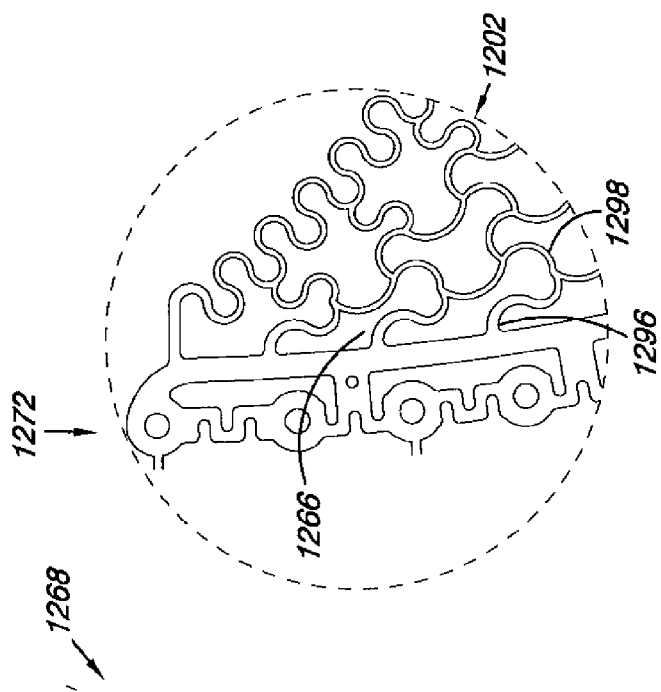
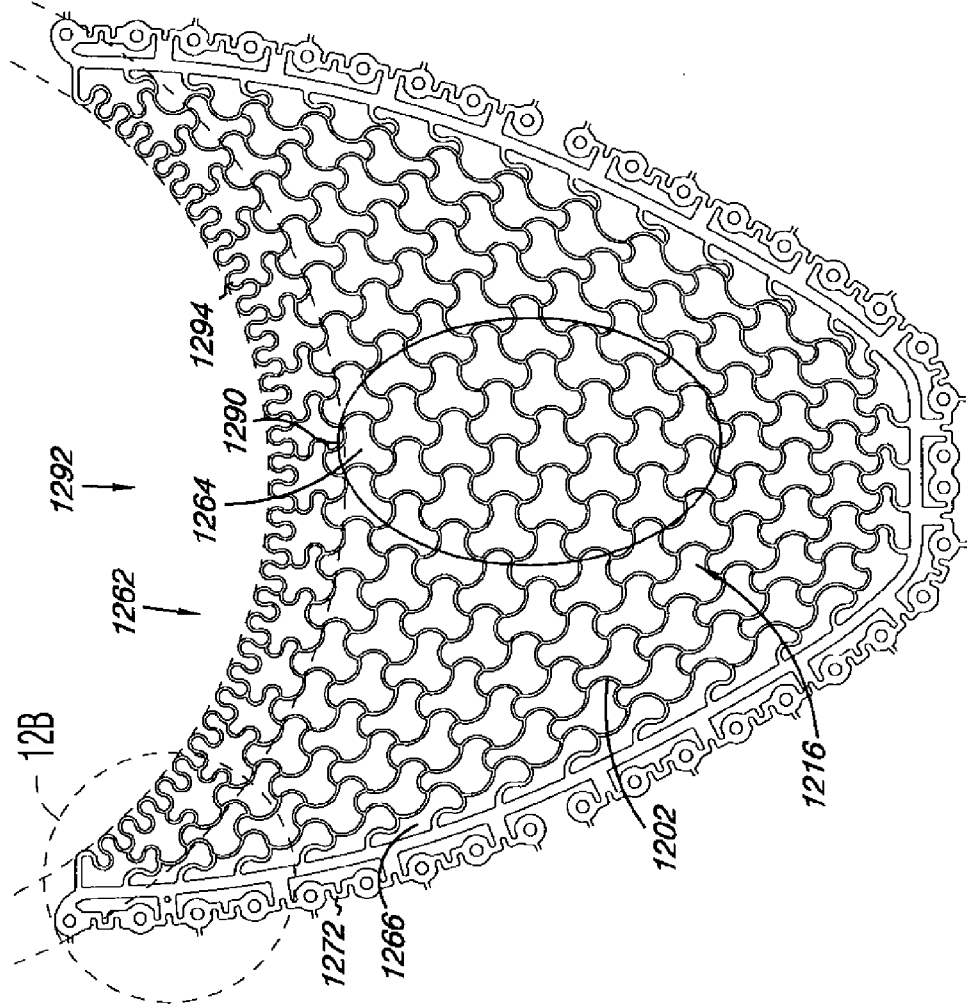
Fig. 12A
Fig. 12B

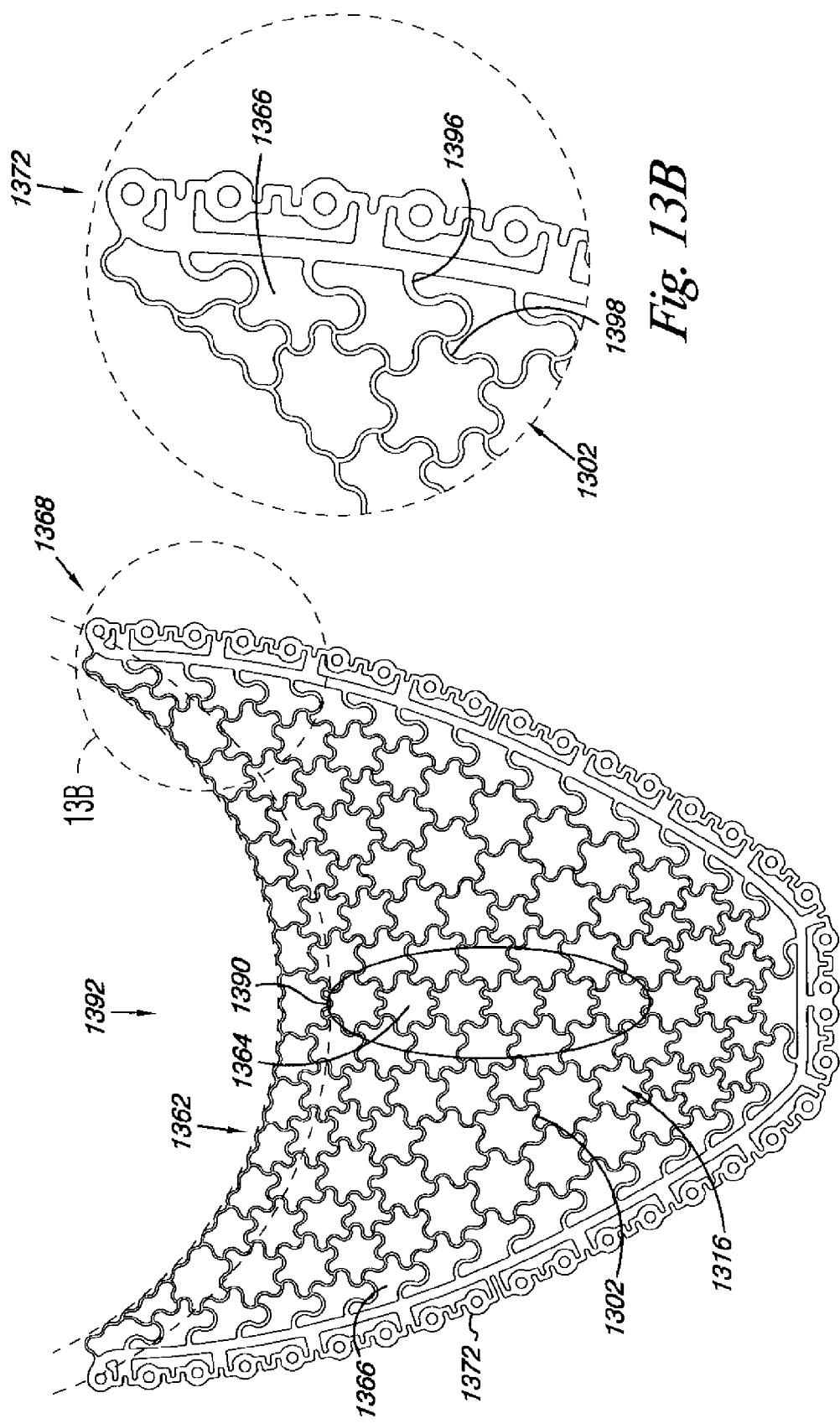

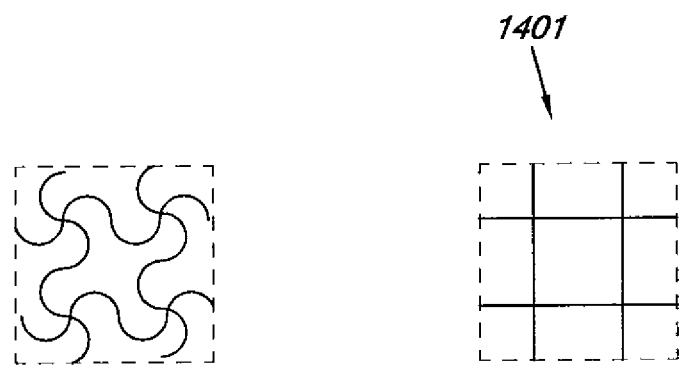
*Fig. 14A*  *Fig. 14B*
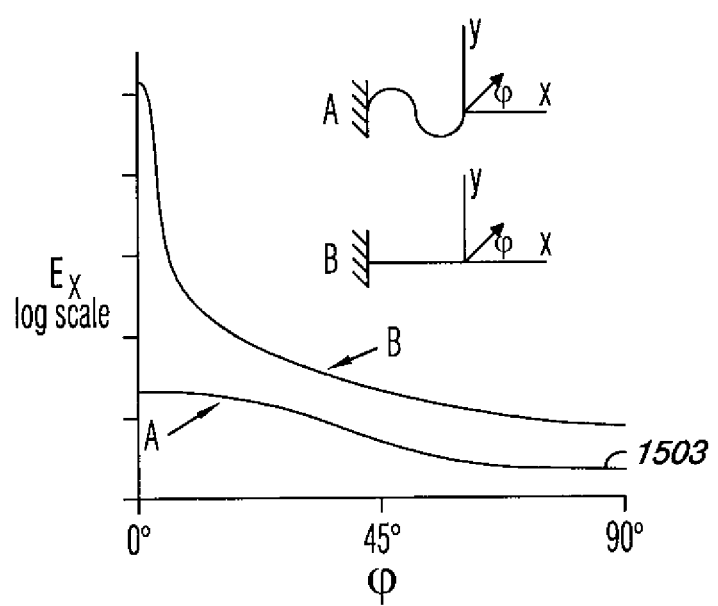
*Fig. 15*

SYNTHETIC COMPOSITE STRUCTURES

This application is a Continuation in Part of U.S. application Ser. No. 12/012,919 filed Feb. 5, 2008, which claims priority from U.S. Provisional Application Ser. No. 60/899,445 filed Feb. 5, 2007, the entire content of which is incorporated herein by reference.

TECHNICAL FIELD

The present disclosure relates to a composite biomaterial with a continuous metal sheet having a polymer layer, a valve frame, and a valve for use with the continuous metal sheet.

BRIEF DESCRIPTION OF THE DRAWINGS

FIG. 11 illustrates an example of a valve leaflet formed from an embodiment of the composite biomaterial according to the present disclosure.

FIG. 12 illustrates an example of a valve leaflet formed from an embodiment of the composite biomaterial according to the present disclosure.

FIG. 13 illustrates an example of a valve leaflet formed from an embodiment of the composite biomaterial according to the present disclosure.

FIGS. 14A-14B illustrate arcuate members (FIG. 14A) and linear beam members (FIG. 14B).

FIG. 15 illustrates modulus versus angle of deformation information for embodiments illustrated in FIGS. 14A and 14B.

DETAILED DESCRIPTION

Figure 1:
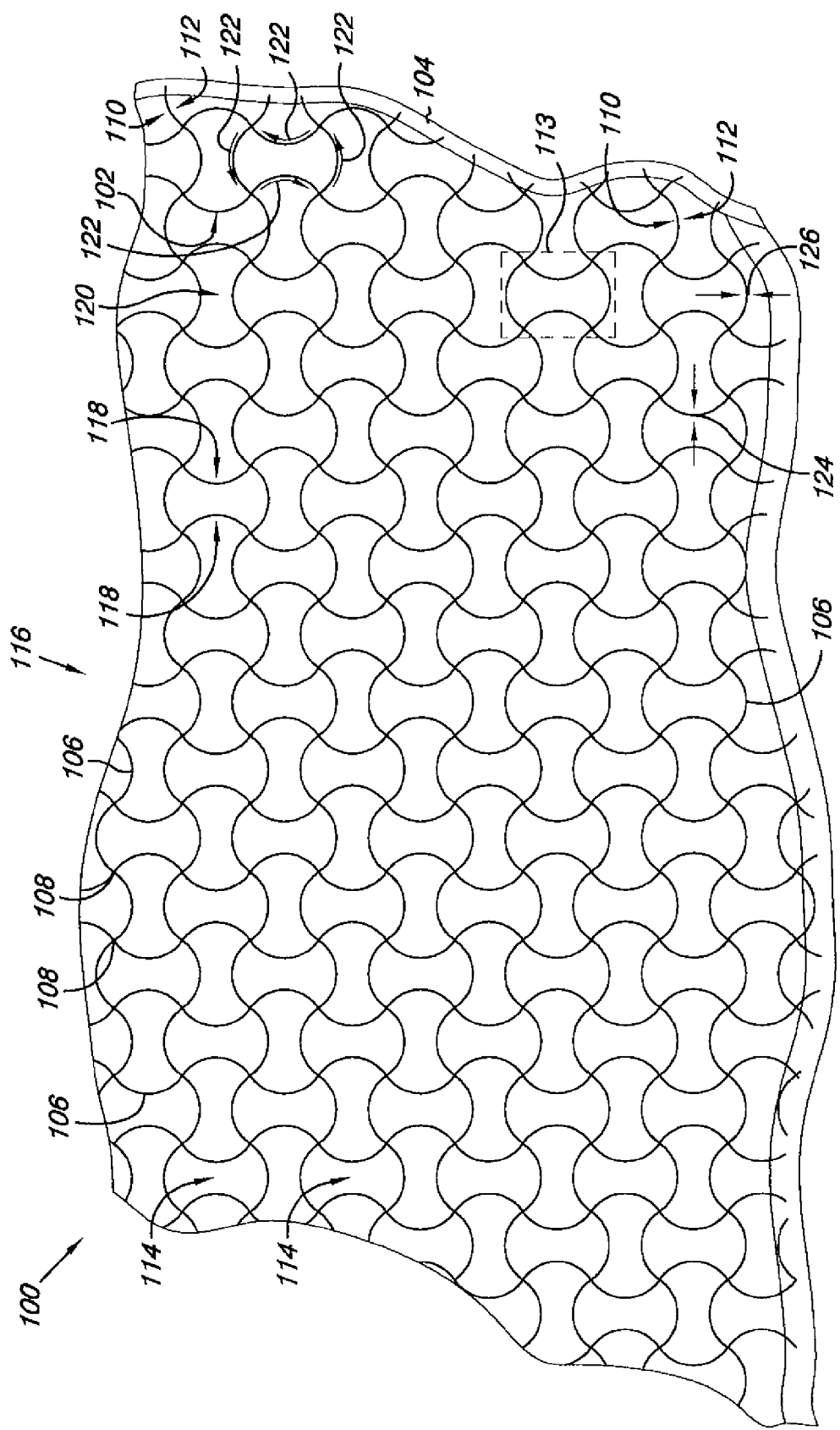
FIG. 1 illustrates an example of a composite biomaterial according to the present disclosure.

Embodiments of the present disclosure are directed to a composite biomaterial, devices and systems that include the composite biomaterial, and method for forming and use of the composite biomaterial. Embodiments of the present disclosure are also directed to a valve frame, a valve, and methods of forming the valve. The valve frame can be used for valve replacement and/or augmentation. In some embodiments, the valve frame can be a device that includes the composite biomaterial of the present disclosure.

The composite biomaterial of the present disclosure includes a continuous metal sheet of material having a predefined fenestration pattern and a polymer layer on at least one surface of the continuous metal sheet.

Embodiments of the composite biomaterial of the present disclosure provide improved mechanical properties that are not available in known materials. For example, the continuous metal sheet of the composite biomaterial does not display fretting and/or shear failure modes, which are both known to occur in existing composite materials. In other words, the continuous metal sheet with the predefined fenestration pattern(s) of the present disclosure does not encounter fretting failure and/or loading failure (polymer matrix to filament failure) that can be found in traditional composite materials. As used herein, the term "fretting" is a failure mode in which independent elements of a material (e.g., a strand and/or a fiber of a woven or knit material) move relative each other so as to cause the elements to wear and/or abrade against each other. In contrast, the continuous metal sheet of material having the predefined fenestration pattern allow for a continuous change of curvature or flexure along more than one axis without undergoing fretting, as will be discussed herein.

For the various embodiments, the predefined fenestration pattern provides the composite biomaterial with the ability to elastically deform in all directions. As a result, the composite biomaterial can, besides other things, elastically stretch to allow a sheet of the composite biomaterial to bend in more than one axis without buckling. As used herein, the term "buckling" means to have a short tight twist, bend or curl caused by a doubling or a winding of the sheet upon itself that forms a line, a mark, a ridge or discontinuity in an otherwise smooth surface. As used herein, a discontinuity in a surface is a location where the curvature of a surface changes abruptly in space and/or time (i.e., where the surface goes from one smoothly changing surface abruptly to another smoothly changing surface) so as to form a buckle in the biomaterial.

As discussed herein, the composite biomaterial combines desirable properties and physical characteristics of each of the continuous metal sheet of material with the predefined fenestration pattern and the polymer layer. In one embodiment, there can be a synergistic effect in the combination of the continuous metal sheet and the polymer layer, as discussed herein. In addition, the composite biomaterial of the present disclosure exhibits complex mechanical properties, discussed herein, which can mimic those found in the in situ biological setting where the composite biomaterial are to be used.

As used herein, the terms "a," "an," "the," "one or more," and "at least one" are used interchangeably and include plural referents unless the context clearly dictates otherwise. Unless defined otherwise, all scientific and technical terms are understood to have the same meaning as commonly used in the art to which they pertain. For the purpose of the present disclosure, additional specific terms are defined throughout.

As used herein, a "composite biomaterial" refers to a material composed of at least one continuous metal sheet of material having at least one of a defined fenestration pattern according to the present disclosure and a polymer layer of the present disclosure on at least one surface of the continuous metal sheet. The composite biomaterial may also include desired a filler, an excipient material, an adjuvant and/or a coating to enhance specific mechanical and/or biological characteristics of the composite material. As used herein a "polymer layer" refers to a synthetic polymer, a non-synthetic polymer, and/or combinations of synthetic and non-synthetic polymers, as will be discussed here.

The polymer layer can be a mixture of one or more of a synthetic and/or one or more of a non-synthetic polymer, where a "mixture" can be defined as the state formed by two or more ingredients that are evenly distributed and/or commingled with each other, but yet retain a separate existence. Alternatively, the polymer layer can be formed in domains of one or more of a synthetic and/or one or more of a non-synthetic polymer, where when two or more domains are used they join along an interface.

As used herein, a "continuous metal sheet" refers to a material having a surface that does not cross over itself and where it is possible to pass from any one point of the surface to any other without leaving the surface. This is in contrast to sheets of material that are formed in a woven or knit pattern, where multiple strands of material are interlaced together. Forming the continuous metal sheet from a continuous piece of material as compared to multiple strands of material eliminates the problem of fretting that can be experienced when the strands of a woven or knit material surface slide over each other.

As appreciated, more than one of the continuous metal sheets of the present disclosure can be used in the composite biomaterial. For example, two or more of the continuous metal sheets can be positioned at least partially on top of each other, where they are spaced apart by the polymer layer. In addition, two or more of the continuous metal sheets can be used as separate sheets in the same device.

Embodiments of the present disclosure provide for fenestration patterns to be formed in a continuous metal sheet through a number of different processes, as will be discussed herein. As used herein a "fenestration pattern" refers to a predefined configuration of apertures (i.e., openings) in the continuous metal sheet, where the apertures are defined by members and junctions from which the members extend.

As used herein "arc" or "arcuate" refer to portions of a curved shape having a locus. In one embodiment, the arc and/or arcuate do not include straight lines or line segments. The curved shape can include, but are not limited to, algebraic curves including, but not limited to, circles, ellipses, hyperbolas, and parabolas, and transcendental curves. Other types of curves are also possible.

Meshes with straight struts display orthotropic material properties. This results in excessive tensile and shear stiffness along some axes. Using arcuate members relaxes the constraints on orthotropic materials thereby enabling smoother changes in surfaces curvature. For example, consider a mesh design that forms a quadrangle parallelogram 1401 (encompassing square, rectangular and diamond shapes) as depicted in FIG. 14B. Note that the linear beams depicted in FIG. 14B can be substituted with arcuate members as shown in FIG. 14A. Deformation of the mesh segments depicted in FIGS. 14A and 14B can be approximated by isolating the behavior of one side of the parallelogram as shown in FIG. 15, Example B. As the segment is deformed along its "x" axis, the modulus in that axis ($E_x$) is defined by the modulus of the material and the resulting stress is very high. Substituting the straight beam with an arcute beam as in Example A reduces the modulus significantly (in this case, the modulus of a stainless steel straight beam would be approximates $2 \times 10^9$ Pa, while an arcuate beam is approximately $6 \times 10^6$ Pa, a change of over 300 times) and results in improved stress behavior that is less dependant on the angle of deformation as shown in Curve A. Note that the curves shown in FIG. 15 are generalizations of beam behavior and are not intended to be quantitative.

In addition, the composite biomaterial of the present disclosure can be further characterized in that it is designed and constructed to be placed in or onto the body or to contact fluid or tissue of the body. The composite biomaterial of the present disclosure will be biostable, biocompatible, and will minimize adverse reactions in the body such as blood clotting, tissue death, tumor formation, allergic reaction, foreign body reaction (rejection) or inflammatory reaction; will have the physical properties such as strength, elasticity, permeability and flexibility required to function for the intended purpose; and can be purified, fabricated and sterilized. A "biostable" material is one that is not broken down by the body, whereas a "biocompatible" material is one that is not rejected by the body.

Composite biomaterials of the present disclosure can be used in a medical device. As used herein, a "medical device" may be defined as a device that has surfaces that contact blood or other body fluids and/or tissues in the course of their operation. This can include, for example, extracorporeal devices for use in surgery such as blood oxygenators, blood pumps, blood sensors, tubing used to carry blood and the like which contact blood which is then returned to the patient. This can also include implantable devices such as vascular grafts, stents, electrical stimulation leads, bladder slings, hernia repair, bowel repair, valve leaflets for use in the cardiovascular system (e.g., heart valves, venous valves), orthopedic devices, catheters, catheter shaft components, proximal and distal protection filters, guide wires, shunts, sensors, membranes, balloons, replacement devices for nucleus pulposus, cochlear or middle ear implants, used in associate with such devices, and the like.

The composite biomaterials of the present disclosure can also be used in non-medical applications. For example, the embodiments of the composite materials discussed herein can be used in any number of applications where thin, tough, flexible, and compliant materials that can undergo out of plane deformations (e.g., prescribed inhomogeneous deformation behavior) are needed. These applications include those of aerospace applications, manufacturing applications, automotive applications, among others.

The figures herein follow a numbering convention in which the first digit or digits correspond to the drawing figure number and the remaining digits identify an element or component in the drawing. Similar elements or components between different figures may be identified by the use of similar digits. For example, 110 may reference element "10" in FIG. 1, and a similar element may be referenced as 210 in FIG. 2. As will be appreciated, elements shown in the various embodiments herein can be added, exchanged, and/or eliminated so as to provide any number of additional embodiments of valve and/or system. In addition, as will be appreciated the proportion and the relative scale of the elements provided in the figures are intended to illustrate the embodiments of the present disclosure (i.e., elements in figures not to scale), and should not be taken in a limiting sense.

FIG. 1 provides an embodiment of a composite biomaterial 100 of the present disclosure. The composite biomaterial 100 includes a continuous metal sheet 102 and a polymer layer 104. As illustrated, both the continuous metal sheet 102 and the polymer layer 104 extend across the entire area of the composite biomaterial 100. In an alternative embodiment, the composite biomaterial 100 can include a predefined zone in which one of either the continuous metal sheet 102 or the polymer layer 104 is present and the other is not present. In other words, the predefined zone is a region in which the continuity of the either of the continuous metal sheet 102 or the polymer layer 104 is interrupted. As appreciated, the composite biomaterial 100 can include more than one of the predefined zones.

For the various embodiments, the continuous metal sheet 102 includes arcuate members 106 that extend from a junction 108. As illustrated, the junction 108 is a location on the continuous metal sheet 102 from which the arcuate members 106 extend to an adjacent junction 108. In one embodiment, the junction 108 is a portion of three or more of the arcuate members 106 being present at one location.

The arcuate members 106 include a first surface 110 and a second surface 112 that define cells 113 having an aperture 114 extending there between in the continuous metal sheet 102. The aperture 114 defined by the arcuate members 106 provide a fenestration pattern 116 in the continuous metal sheet 102. Forming the fenestration pattern 116 in the continuous metal sheet 102 can be accomplished by a number of different techniques. These techniques can include laser cutting, water jet cutting, photolithography techniques, abrasive cutting, etching techniques, among others. The continuous metal sheet 102 with the fenestration pattern 116 can be smoothed and/or polished using known methods.

As illustrated, the fenestration pattern 116 includes a repeated series of apertures 114. In one embodiment, this repeated series of apertures 114 can be arranged in a uniform, regular and symmetrical pattern relative the junction 108. So, the repeated series of the apertures 114 of the fenestration pattern 116 have the same shape (i.e., form), arranged in the same pattern, and each having the same surface area. In other words, the fenestration pattern 116 is homogenous pattern In an alternative embodiment, the fenestration pattern 116 can include a repeated series of the apertures having two or more different shapes, where each of the two or more shapes either has or does not have the same surface area. In one embodiment, the two or more different shapes can be arranged systematically to provide one or more of a repeated block of the two or more shapes where the blocks are used to form the fenestration pattern. So, for example the two or more different shapes could be arranged in a predefined block pattern that repeats in series to form the fenestration pattern. Alternatively, the two or more different shapes can be arranged randomly to form the fenestration pattern. As a result, the repeated series of apertures could have a non-uniform configuration, with an irregular arrangement and/or a non-symmetrical pattern relative a junction. In other words, the fenestration pattern is heterogeneous pattern.

As illustrated, the arcuate members 106 each have a single arc shown generally at 118 that extends between adjacent junctions 108. Each of the arcuate members 106 can also include more than one arc between the adjacent junctions 108, as will be discussed herein. For the various embodiments, the single arc 118 can have a number of different shapes of curvature and/or curvature vectors (e.g., the sharpness of the curve). For example, the single arc 118 can have an elliptical curvature. Alternatively, the single arc 118 can have a circular curvature. Other shapes are also possible, including but not limited to sinusoidal curvature, and cubic spline curvature, among others described herein.

In addition, for the various embodiments each of the apertures 114 can also include a center of symmetry 120 (i.e., a centroid) around which the arcuate members 106 extend in a series of alternating directions. So for example, the direction of curvature alternates (shown generally at 122) for each arcuate member 106 in a series of members extending around the center of symmetry 120 to define one of the apertures 114.

For the various embodiments, the arcuate members 106 with junctions 108 provide the continuous metal sheet 102 with the ability to elastically stretch as a result of flexure (i.e., elastic bending or stretching) of the arcuate members 106 in response to an applied net force of compression and/or tension. For the various embodiments discussed herein, the continuous metal sheet 102 can elastically stretch along any direction in which the arcuate members 106 travel. This characteristic of the arcuate members 106 allows the continuous metal sheet 102 to shear deform in all directions. In addition, the arcuate members 106 also allow the continuous metal sheet 102 to stretch in any direction along which the junctions 108 are aligned.

For the various embodiments discussed herein, the continuous metal sheet helps to provides torsional coupling between arcuate members of the continuous metal sheet and the polymer layer that is not provided in composite materials having fabric and/or fibrous reinforcements. The arcuate members of the continuous metal sheet maintain torsional coupling with the polymer layer, which helps to reduce the shear stress between the polymer layer and continuous metal sheet. This is not the case with composite materials having fabric and/or fibrous reinforcements. In fibrous composite materials, mechanical coupling is provided through the polymer matrix in which they are embedded. So, while the tensile loads may be carried by the fibers, the torsional loads are carried by the polymer matrix. When under a torsional load it is the interface between the fibrous material and the polymer matrix bears the load, and this is where the failure can occurs. The biomaterial composites of the present disclosure do not share this problem.

The response of the continuous metal sheet 102 to an applied net force is in contrast to other possible support sheets formed from non-arcuate members (i.e., straight members). In a support sheet formed with straight members (e.g., a diamond shaped repeating pattern, etc) there are axes along which the support sheet will not elastically stretch or shear. These can include the axes along which both the straight members and their junctions align to form what is essentially a column. A support sheet having such a structure will neither elastically stretch nor compress in all directions of loading (i.e., will not shear deform in all directions). As appreciated, there may be an insignificant amount of stretch in such straight members, hut the continuous metal sheet of the present disclosure elastically stretches magnitudes more as compared to support sheets formed with non-arcuate members.

In addition, support sheets with straight members as discussed herein cannot bend in more than one orthogonal axis without buckling. As used herein, the term "buckling" means to have a short tight twist, bend or curl caused by a doubling or a winding of the sheet upon itself that forms a line, a mark or a ridge in an otherwise smooth surface. This can occur in the support sheets with straight members when the straight members bend under a compressive force imposed by moving the sheet in more than one axis. As the straight members bend they create a wrinkle (i.e., a ridge or crease) in the curved surface of the support sheet. This disruption in the curved surface can, in applications where the material is in contact with blood flow, be less than desirable. Examples of such applications include, but are not limited to, vascular applications where smooth continuous surfaces without disruptions (e.g., wrinkles) would be preferred for a number of hemodynamic reasons.

The composite biomaterial 100 of the present disclosure, in contrast, can deform about two or more orthogonal axes without buckling. For the various embodiments, the composite biomaterial 100 has the ability to both maintain continuous curvature in more than one axis while supporting changes in curvature in more than one dimension without forming surface disruptions (e.g., wrinkling, buckling or creasing). For the various embodiments, this is because the arcuate members 106 can elastically stretch to allow the continuous metal sheet 102 to bend in more than one orthogonal axis (e.g., three-dimensions) without buckling. In addition to not buckling, the continuous metal sheet 102 can also deform about two orthogonal axes to provide a continuous smooth curvature across a surface of the polymer layer. In other words, the biomaterial 100 can bend or flex under an applied net force without developing wrinkles and/or interruptions in a path projected by the surface.

As will be appreciated, there are a number of parameters of the continuous metal sheet 102 that can be modified to adjust the characteristics and/or behaviors of the biomaterial 100 under stress. For example, changes to the shapes of curvature and/or curvature vectors (e.g., the sharpness of the curve), dimensions (e.g., changes in width and/or thickness) of the members 106 and/or the junctions 108 can be used to modify and/or adjust, for example, the stiffness, compliance, and/or flexibility dynamic response of the biomaterial 100.

In an additional embodiment, the continuous metal sheet 102 can also include members that are straight, in addition to those that are arcuate, as described herein. In one embodiment, use of straight members in addition to the arcuate members can be useful in applications that require planar structures and/or bending on only one axis.

For the various embodiments, the arcuate members 106 can have a width 124 and/or a thickness 126 of less than 0.127 mm. In an additional embodiment, the arcuate members 106 can have a width 124 and/or a thickness 126 of less than 0.0762 mm. Alternatively, the width 124 and/or the thickness 126 can be from 0.254 millimeter to 0.127 millimeter. The width 124 and/or the thickness 126 could also be 0.127 to 0.0127 millimeter. In a specific embodiment, both the width 124 and the thickness 126 are 0.0254 millimeter or less. Other values for the width and/or thickness are also possible and their value(s) can depend upon the application and/or desired function of the composite biomaterial of the present disclosure.

In an additional embodiment, the cross-sectional shape and/or size of the members 106 and/or junctions 108 can be used to modify the characteristics and/or behaviors of the biomaterial 100 under stress. For example, the members 106 and/or junctions 108 can have similar and/or different cross-sectional geometries along their length. The similarity and/or the differences in the cross-sectional geometries can be based on one or more desired functions to be elicited from each portion of the members 106, the junctions 108 and/or the portion of the continuous metal sheet 102. Examples of cross-sectional geometries include rectangular, non-planar configuration, round (e.g., circular, oval, and/or elliptical), polygonal, and arced. Other cross-sectional geometries are possible.

In one embodiment, the modifications discussed herein can be made to the entire continuous metal sheet 102. Alternatively, the modifications discussed herein can be made in one or more discrete regions of the continuous metal sheet 102. For example, a first region can have members 106 and/or junctions 108 of a first thickness, width and/or cross sectional shape while a second region different than the first can have members 106 and/or junctions 108 of a second thickness, width and/or shape. Such modifications can also occur for the members 106 and junctions 108 defining individual apertures 114. In other words, the modifications can occur for one or more of the individual apertures 114.

In addition, the selection of material used to form the continuous metal sheet 102 can also be used to determine the characteristics and/or behaviors of the biomaterial 100. For example, the continuous metal sheet 102 can be formed of a metal or a metal alloy having sufficient mechanical properties to resist fatigue. Examples of such metals and/or metal alloys include Tantalum, Stainless Steel alloys platinum enriched stainless steel (PERSS, 304, 316, 17-7 PH, 17-4 PH), Tungsten, Molybdenum, Cobalt Alloys such as MP35N, Elgiloy and L605, Nb-1Zr, platinum, gold, rhodium, iridium oxide, Nitinol, Inconel and titanium, among others.

Additional examples of suitable metals and metal alloys include those having no grain structure or small grain structure that is less than about 5 microns. An example of such a metal includes those sold under the trade designator "Metglas" (Metglas®, Inc. Conway, S.C.). Other metal and metal alloys are also possible.

The polymer layer 104 can also be used in tailoring the characteristics and/or behaviors of the biomaterial 100 under stress. For example, the polymer layer 104 can have anisotropic tensile properties that can be used to modify the mechanical properties of the biomaterial 100. These anisotropic tensile properties can be determined by the chain structure and configuration, orientation, cross-linking, and molecular weight, among others, of the polymer layer 104.

For the various embodiments, examples of oriented polymers include those that are uniaxial oriented, biaxial oriented, or multi-axial oriented. As understood, an oriented polymer has been processed (e.g., stretched and/or compressed) to align the molecular structures (e.g., the polymer chains) along at least one principle axis. Uniaxial-oriented polymers have been oriented along one axis, while biaxial-oriented polymers have been aligned along two orthogonal axes (e.g., a biaxially planar oriented structure). Typically, an oriented polymer is less flexible along the axis of orientation as compared to an axis of non-orientation.

Examples of biaxially oriented polymers include those polymers that were initially isotropic and then were stretched simultaneously in two orthogonal directions to deform in all in-plane directions. Specific examples include blown polymer films having a slight shear induced orientation that are then expanded with a gas to stretch the material many fold in all directions simultaneously. The result can be a material having a circular and/or a slightly elliptical distribution of orientation and modulus. Alternatively, the biaxial-oriented polymer can also include those polymers that have been first stretched in one direction, causing first orientation changes, and then stretched in the other direction to produce a material with orientation in 2 directions (i.e., biaxial orientation).

In an additional embodiment, the polymer layer 104 can be a laminated polymer material having a combination of layers that can each have a different orientation. These polymer materials are sometimes referred to as cross-ply laminates.

In one embodiment, the direction of orientation of the polymer layer 104 can be aligned in a predetermined direction relative the fenestration pattern 116 of the continuous metal sheet 102. For example, the orientation of the polymer layer 104 can be aligned or parallel with rows, columns, and/or diagonals of the junctions 108 of the fenestration pattern 116. Alternatively, the orientation of the polymer layer 104 can be off-set from (i.e., not aligned) the rows, columns, and/or diagonals of the junctions 108 of the fenestration pattern 116. As appreciated, different relative positions of the orientation of the polymer layer 104 and the fenestration pattern 116 can result in a variety of characteristics and/or behavior modifications of the biomaterial 100 under stress.

The polymer layer 104 can be formed from a number of different synthetic and non-synthetic polymers. In one embodiment, the polymer layer 104 can be derived from autologous, allogeneic or xenograft material. As will be appreciated, sources for xenograft material include, but are not limited to, mammalian sources such as porcine, equine, and sheep. Additional biologic materials from which to form the polymer layer 104 include, but are not limited to, explanted veins, pericardium, facia lata, harvested cardiac valves, bladder, vein wall, various collagen types, elastin, intestinal submucosa, and decellularized basement membrane materials, such as small intestine submucosa (SIS), amniotic tissue, or umbilical vein.

Alternatively, the polymer layer 104 could be formed from a synthetic material. The synthetic material can be formed in a manner that enhances the porosity of the material so as to improve biocompatibility of the material. Examples of such techniques include expansion, electrospinning, braiding, knitting or weaving of the material. In one embodiment, the synthetic material can have a balance of porosity such that it provides a preferable surface for cellular activity while minimizing fluid, i.e., blood, passage through it.

Examples of such synthetic materials include, but are not limited to, fluorpolymers such as expanded polytetrafluoroethylene (ePTFE) and polytetrafluoroethylene (PTFE), elastomers such as polystyrene-polyisobutylene-polystyrene (SIBS), polyester, polyethlylene (PE), polyethylene terephthalate (PET), polyimides, silicones, polyurethanes, segmented poly(carbonate-urethane), polyurethane ethers, polyurethane esters, polyurethaneureas and the like, as well as mixtures and copolymers thereof. The use of biodegradable polymers and electrospun polymers (biodegradable or not) are also possible.

An excipient material may optionally be added to the polymer layer 104 of the composite biomaterial 100. In one embodiment, the excipient can be a material that will temporarily fill the porosity of the porous polymer to enhance the ability to prevent fluid flow through the pores. An example of such a filler is variations of polyethylene glycol that is well tolerated in vivo and may dissolve at slow or fast rates depending on molecular weight. The excipient may also have a biologically active role to enhance function of the material. For example, coatings containing proteins and/or peptides could be used to create favorable conditions for endothelial cells to spread on a surface and enhance healing. Similarly, a coating of heparin or other thromboactive materials could reduce the potential for fibrin deposition on the leaflet surface.

An example of a suitable synthetic material can be found in U.S. patent application Ser. No. 10/200,997, filed Jul. 23, 2002 and entitled "Conformal laminate stent device"; and U.S. patent application Ser. No. 10/012,919, filed Oct. 30, 2001 and entitled "Green fluoropolymer tube and endovascular prosthesis formed using same," which are both incorporated herein by reference in their entirety.

For the various embodiments, the polymer layer 104 is applied over at least one of the first and/or second surface 110, 112 of the continuous metal sheet 102. In one embodiment, the polymer layer 104 can be provided over both the first and second surface 110, 112 of the continuous metal sheet 102. Alternatively, the polymer layer 104 can be provided over one of the first and second surface 110, 112 of the continuous metal sheet 102.

For the various embodiments, the polymer layer 104 can be joined to the continuous metal sheet 102 using a number of techniques. Such techniques include, but are not limited to, heat sealing, solvent bonding, adhesive bonding or use of coatings. For example, sufficient pressure and heat can be used to cause adherence of the layers (e.g., fusing) together at their points of contact through the apertures 114 in the continuous metal sheet 102. Alternatively, adherence of the polymer layer(s) 104 to the continuous metal sheet 102 can be accomplished by using an adhesive and/or solvent system to soften or dissolve the surface of one or more of the polymer layer(s) 104 and permit commingling of the layers which results in adherence. Other means of affixing the layers to one another are also contemplated and can be found in U.S. patent application Ser. No. 10/200,997, filed Jul. 23, 2002 and entitled "Conformal laminate stent device," which is incorporated herein by reference in its entirety.

As will be appreciated, the polymer layer 104 can be treated and/or coated with any number of surface or material treatments. Examples of such treatments include, but are not limited to, bioactive agents, including those that modulate thrombosis, those that encourage cellular ingrowth, throughgrowth, and endothelialization, those that resist infection, and those that reduce calcification.

Figure 2:
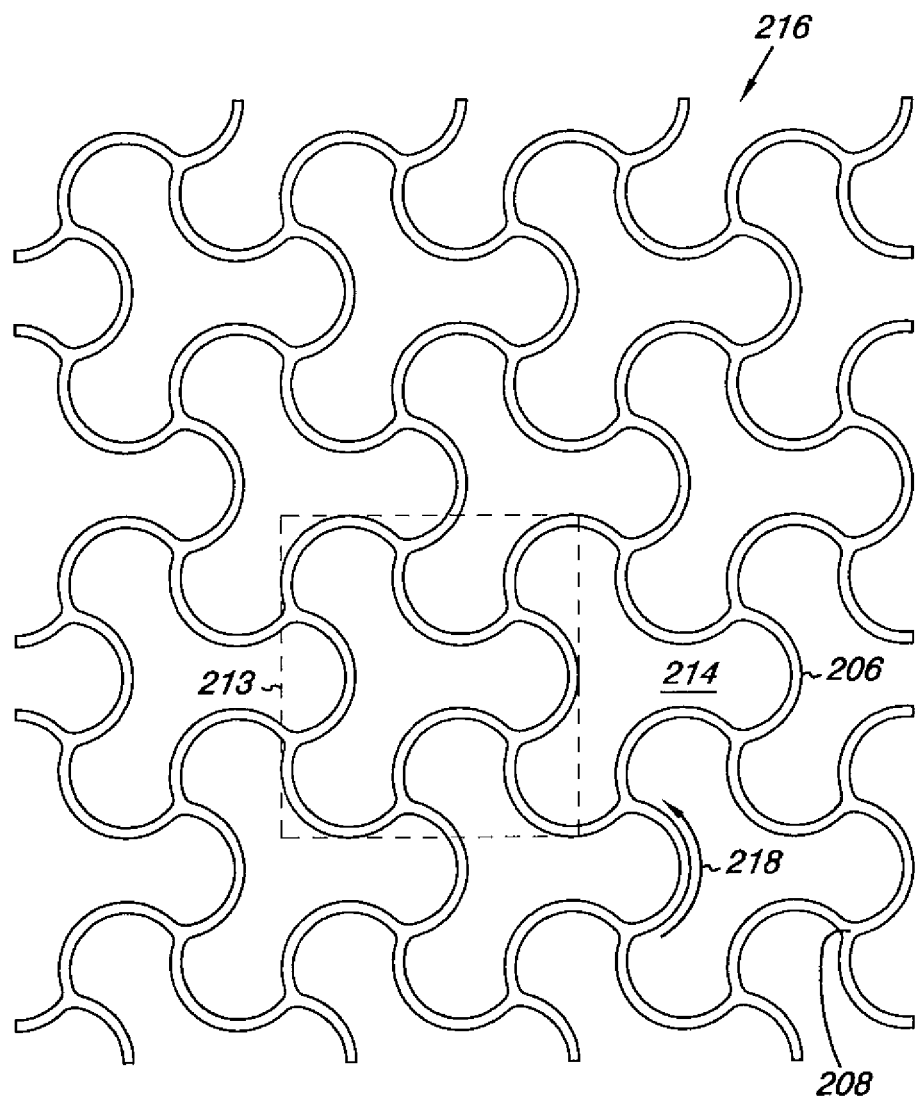
FIG. 2 illustrates an example of a continuous metal sheet of the composite biomaterial according to the present disclosure.

Embodiments of the present disclosure also include a number of different aperture configurations used to form additional fenestration patterns. For example, FIG. 2 provides an additional embodiment of the continuous metal sheet 202 for use in the composite biomaterial according to the present disclosure. As illustrated, the continuous metal sheet 202 includes arcuate members 206 that extend from the junction 208 to define cells 213 having apertures 214 in the fenestration pattern 216.

As with the fenestration pattern illustrated in FIG. 1, the fenestration pattern 216 includes arcuate members 206 having a single arc 218. In contrast to FIG. 1 however, each of the apertures 214 is defined by a greater number of the arcuate members 206 as compared to the number illustrated in FIG. 1. As illustrated, six (6) of the arcuate members 206 define one of the apertures 214, while four (4) of the arcuate members define one of the apertures illustrated in FIG. 1. It is appreciated that other numbers of arcuate members could be used to define the apertures of the fenestration pattern. Such numbers could include three (3), five (5), seven (7), and/or eight (8) among other numbers.

Figure 3:
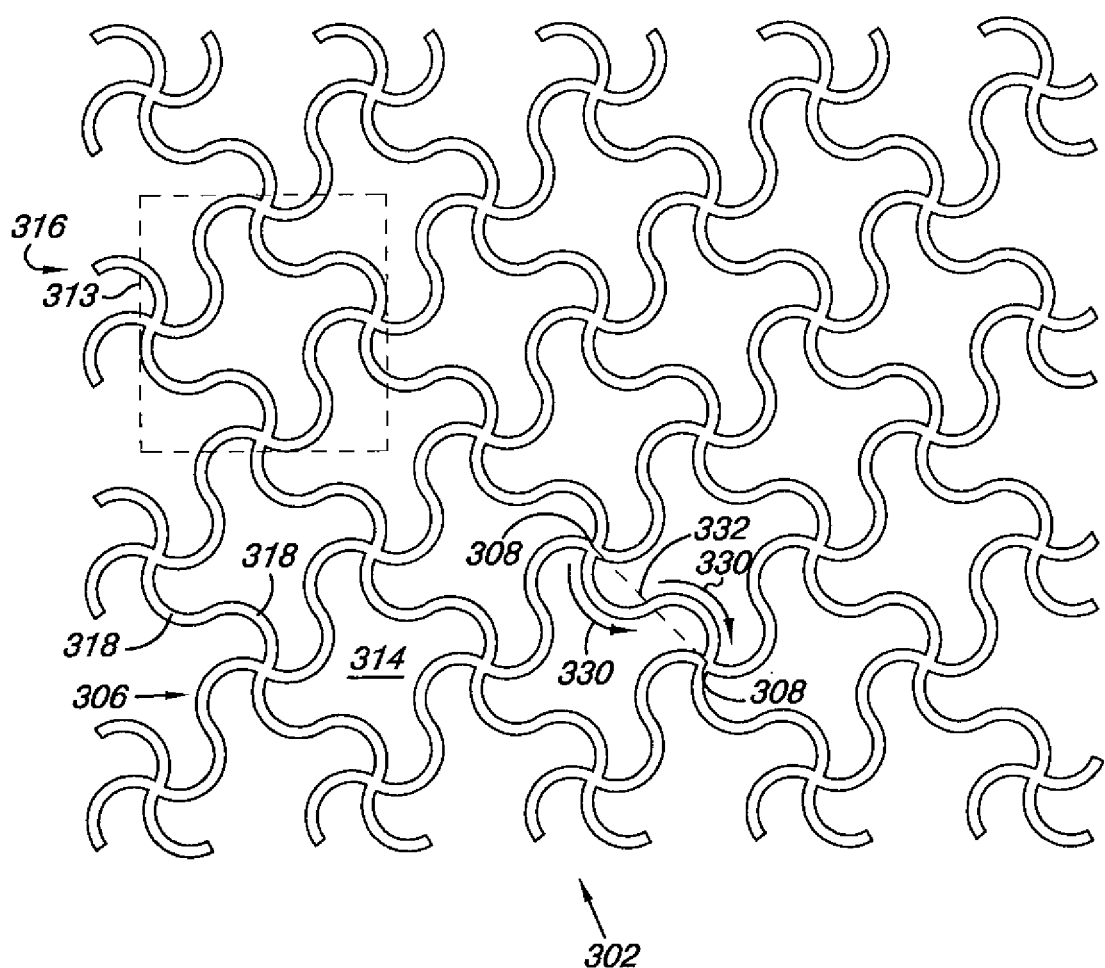
FIG. 3 illustrates an example of a continuous metal sheet of the composite biomaterial according to the present disclosure.

FIG. 3 illustrates another embodiment of the continuous metal sheet 302 for use in the composite biomaterial according to the present disclosure. As illustrated, the continuous metal sheet 302 includes arcuate members 306 that extend from the junction 308 to define cells 313 having apertures 314 in the fenestration pattern 316.

The arcuate members 306 of the present embodiment each define two of the are 318. In other words, each arcuate member 306 extending from a junction 308 defines two of the arc 318 each having different directions of curvature before terminating at the next junction 308. For example, each of the two arcs of the arcuate member 306 extend in opposite directions 330 from a straight line 332 between a pair of adjacent junctions 308. In one embodiment, each of the two arcs 318 of the arcuate member 306 bisects the straight line 332 between a pair of adjacent junctions 308.

In addition to having different directions of curvature, the arcs of the arcuate members 306 can also have variety of different lengths, different shapes of curvature and/or curvature vectors, as discussed herein. For example, the two arcs 318 of each arcuate member 306 can have an equal length. Alternatively, the two arcs of each arcuate member 306 can have an unequal length. In addition, each of the two arcs of the arcuate member 306 can have a number of different curvature shapes, as discussed herein. Alternatively, each of the two arcs of an arcuate member 306 could have different curved shapes selected from those discussed herein.

Figure 4:
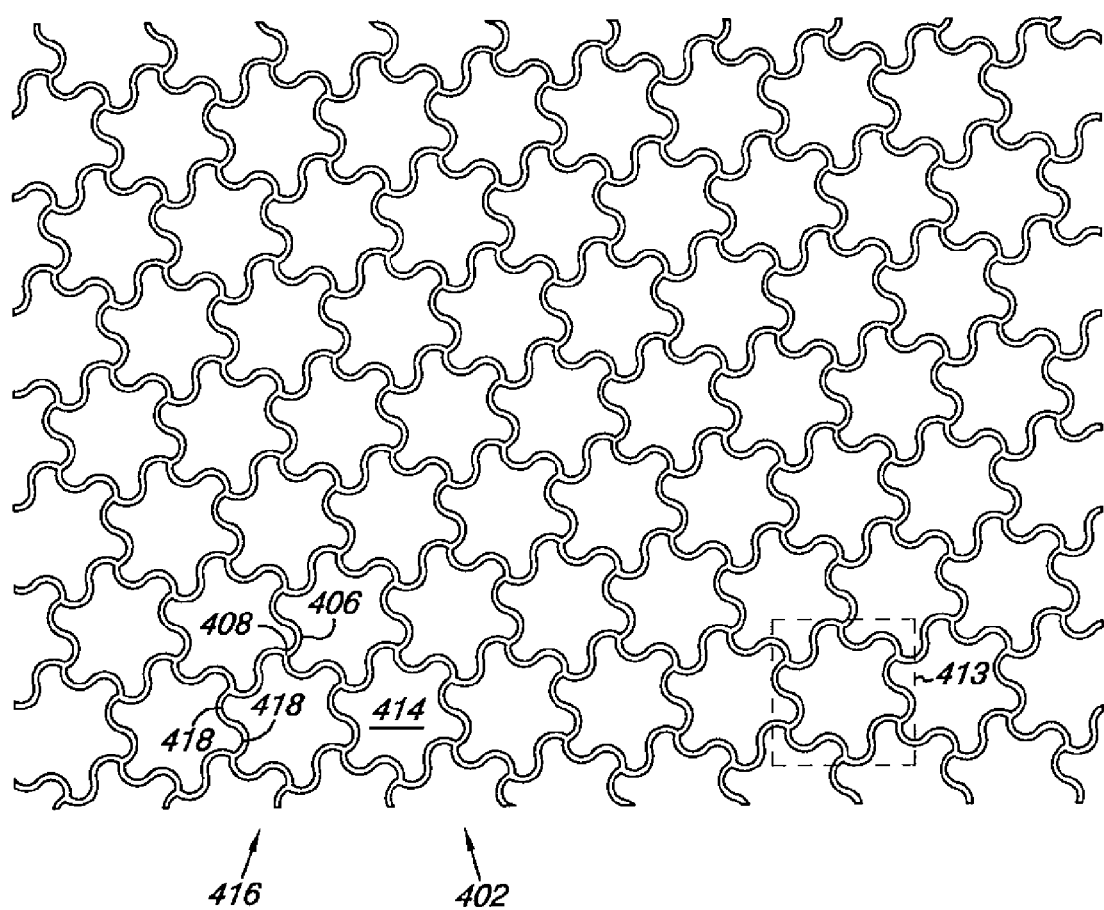
FIG. 4 illustrates an example of a continuous metal sheet of the composite biomaterial according to the present disclosure.

FIG. 4 provides an additional embodiment of the continuous metal sheet 402 for use in the composite biomaterial according to the present disclosure. As illustrated, the continuous metal sheet 402 includes arcuate members 406 that extend from the junction 408 to define cells 413 having apertures 414 in the fenestration pattern 416.

As with the fenestration pattern illustrated in FIG. 3, the fenestration pattern 416 includes arcuate members 406 each defining two arcs 418. In contrast to FIG. 3 however, the apertures 414 are defined by a greater number of the arcuate members 406 as compared to the number illustrated in FIG. 3. As illustrated, six (6) of the arcuate members 406 define one of the apertures 414, while four (4) of the arcuate members define one of the apertures illustrated in FIG. 3. It is appreciated that other numbers of arcuate members could be used to define the apertures of the fenestration pattern, as discussed herein. In addition, the arcs of the arcuate members 406 can also have variety of different lengths, shapes, and/or vectors of curvature, as discussed herein.

Figure 5:
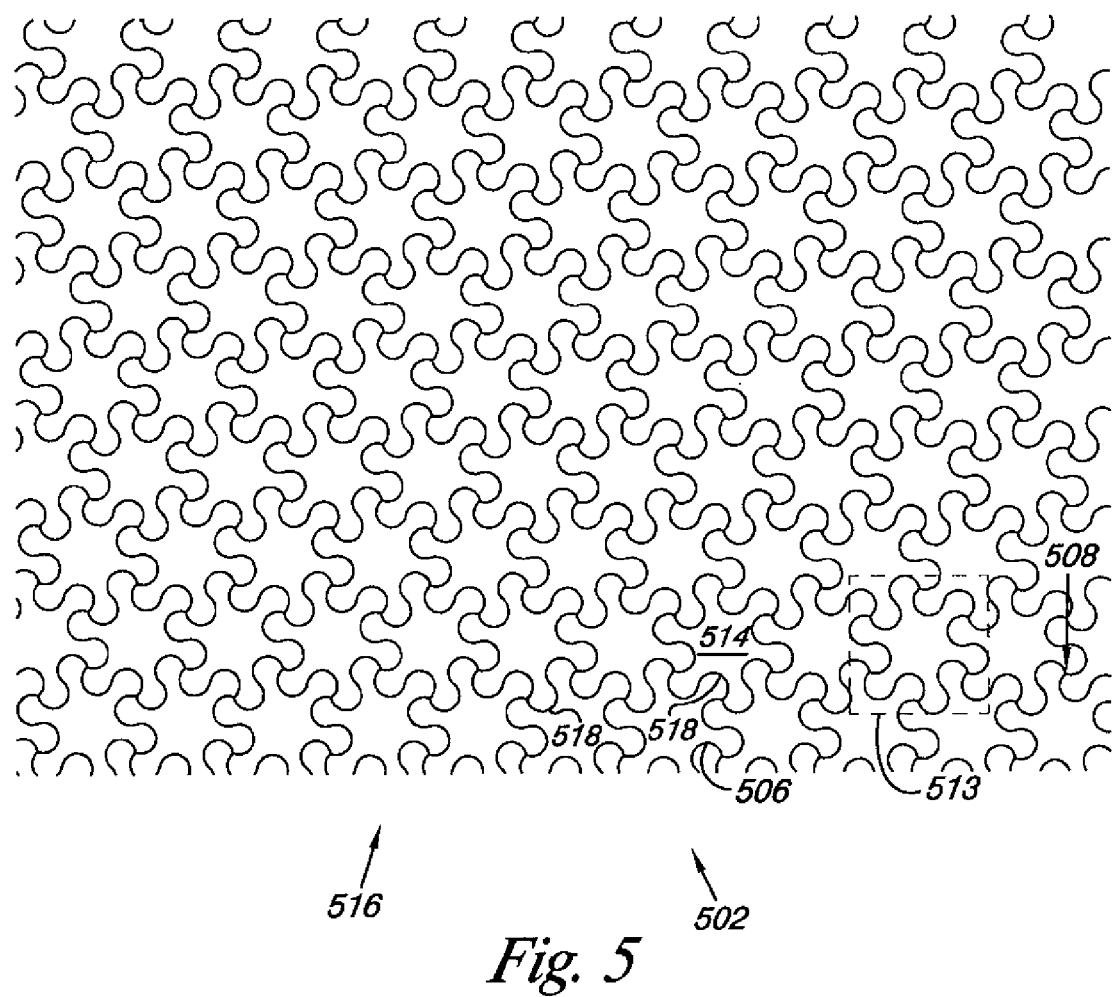
FIG. 5 illustrates an example of a continuous metal sheet of the composite biomaterial according to the present disclosure.

FIG. 5 provides another embodiment of the continuous metal sheet 502 for use in the composite biomaterial according to the present disclosure. As illustrated, the continuous metal sheet 502 includes arcuate members 506 that extend from the junction 508 to define cells 513 having apertures 514 in the fenestration pattern 516. The fenestration pattern 516 includes arcuate members 506 each defining two of the arcs 518. In contrast to FIG. 4 however, the arc length and curvature vectors (e.g., radius of curvature) of the arcs 518 are greater as compared to the arc length and curvature vectors of the arc illustrated in FIG. 4.

Figure 6:
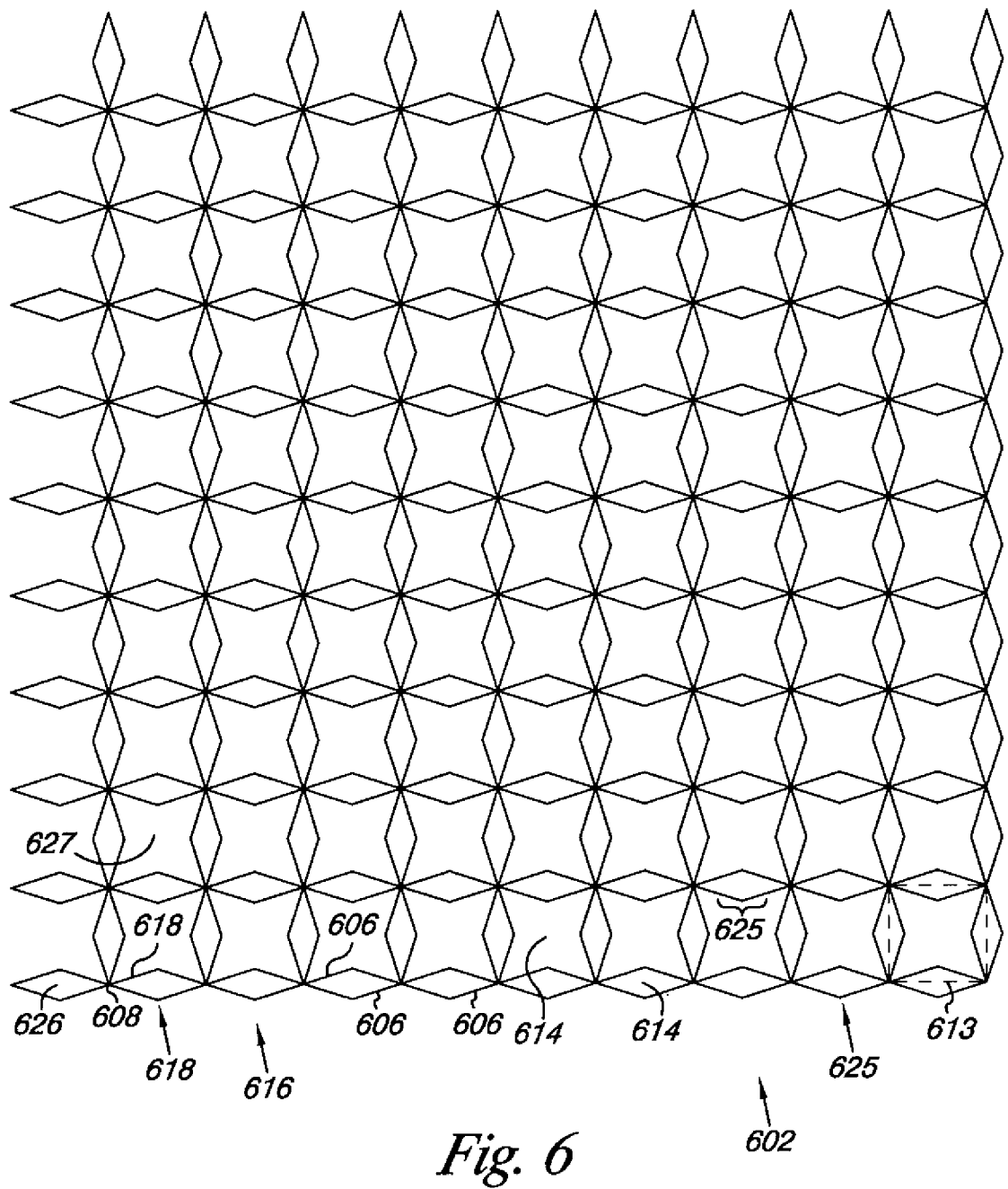
FIG. 6 illustrates an example of a continuous metal sheet of the composite biomaterial according to the present disclosure.

FIG. 6 provides an additional embodiment of the continuous metal sheet 602 for use in the composite biomaterial according to the present disclosure. As illustrated, the continuous metal sheet 602 includes arcuate members 606 in which the members 606 form an angle 625. This is in contrast to a smooth curve as illustrated for other arcuate members discussed herein.

In addition, FIG. 6 also illustrates an embodiment of the continuous metal sheet in which the cells 613 having apertures 614 of the fenestration pattern 616 have two different shapes and sizes, as discussed herein. For example, the fenestration pattern 616 includes a first cell 626 and a second cell 627, where the first cell 626 has a different shape and size (e.g., area) as compared to the second cell 627.

Figure 7:
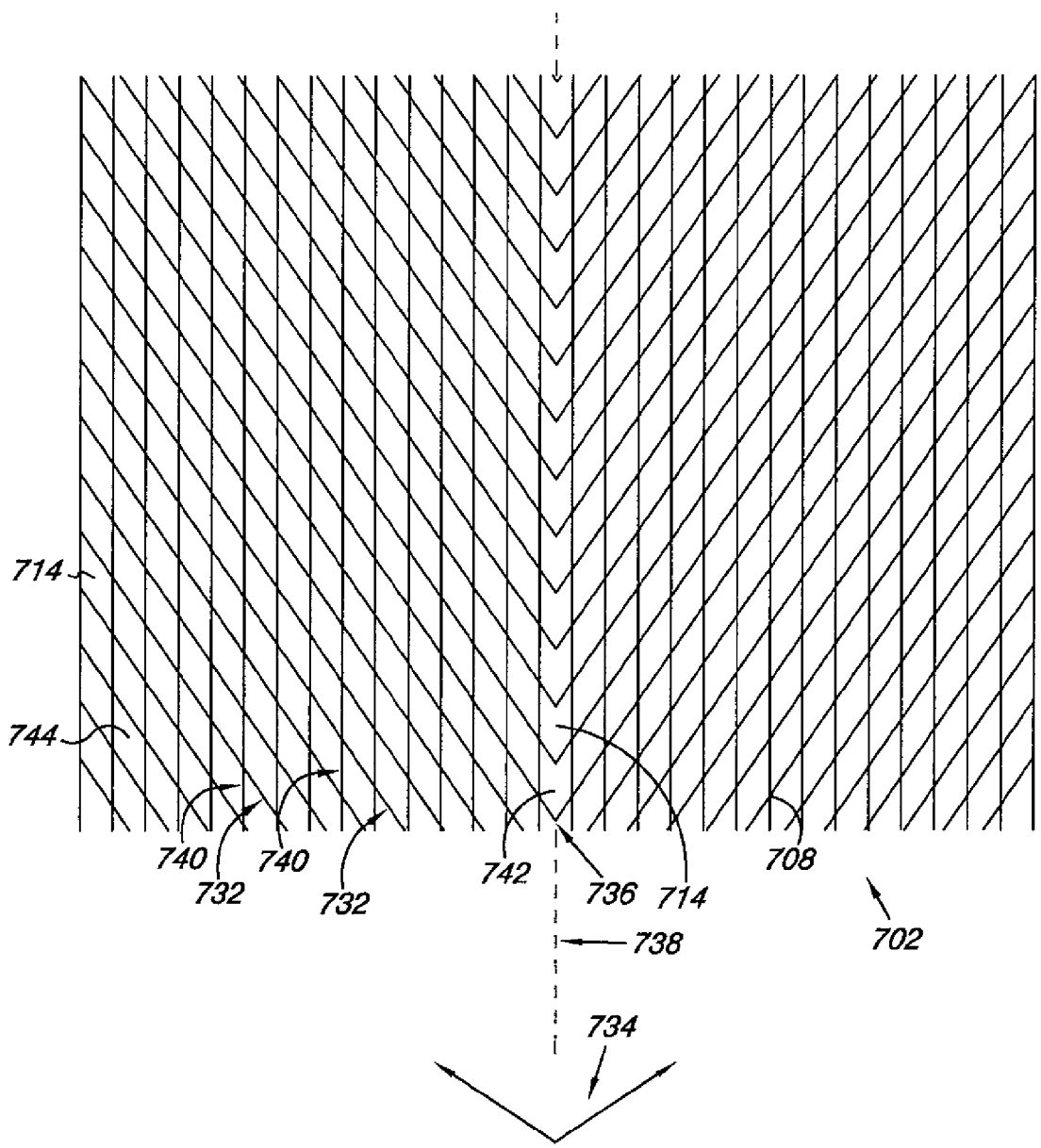
FIG. 7 illustrates an example of a continuous metal sheet of the composite biomaterial according to the present disclosure.

FIG. 7 provides an illustration of an additional continuous metal sheet 702 use in the composite biomaterial according to the present disclosure. As illustrated, the continuous metal sheet 702 includes a first set of members 732 that extend in a radiating pattern 734 from a corner 736 of each of the members 732.

For the various embodiments, the corner 736 of each of the first set of members 732 can be aligned along a center axis 738. In one embodiment, the radiating pattern 734 of the members 732 aligned along the center axis provides a chevron pattern to the members 732. The continuous metal sheet 702 also includes second set of members 740 that extend to intersect the first set of members 732 at junctions 708. As illustrated, the first set of members 732 and the second set of members 740 have a linear shape.

As illustrated, the continuous metal sheet 702 includes apertures 714 defined by the members 732 and 740 that have at least two different shapes. For the present embodiment, the first set of members 732 and the second set of members 740 define a center cell 742 that, in the present embodiment, contains the corner 736. The first set of members 732 and the second set of members 740 also define a unit cell 744 that has a different configuration than the center cell 742. In one embodiment, the center axis 738 provides an axis of symmetry for the first set of members 732 and the second set of members 740.

As illustrated, each center cell 742 of the continuous metal sheet 702 has six sides defined by two of the first set of members 732 and two of the second set of members 740. In the present embodiment, the center cell 742 has a configuration of a concave hexagon. In contrast, the unit cell 744 has four sides defined by the two of the first set of members 732 and two of the second set of members 740. For the various embodiments, the unit cell 744 can have the shape of a rhomboid and/or a rhombus.

Figure 8:
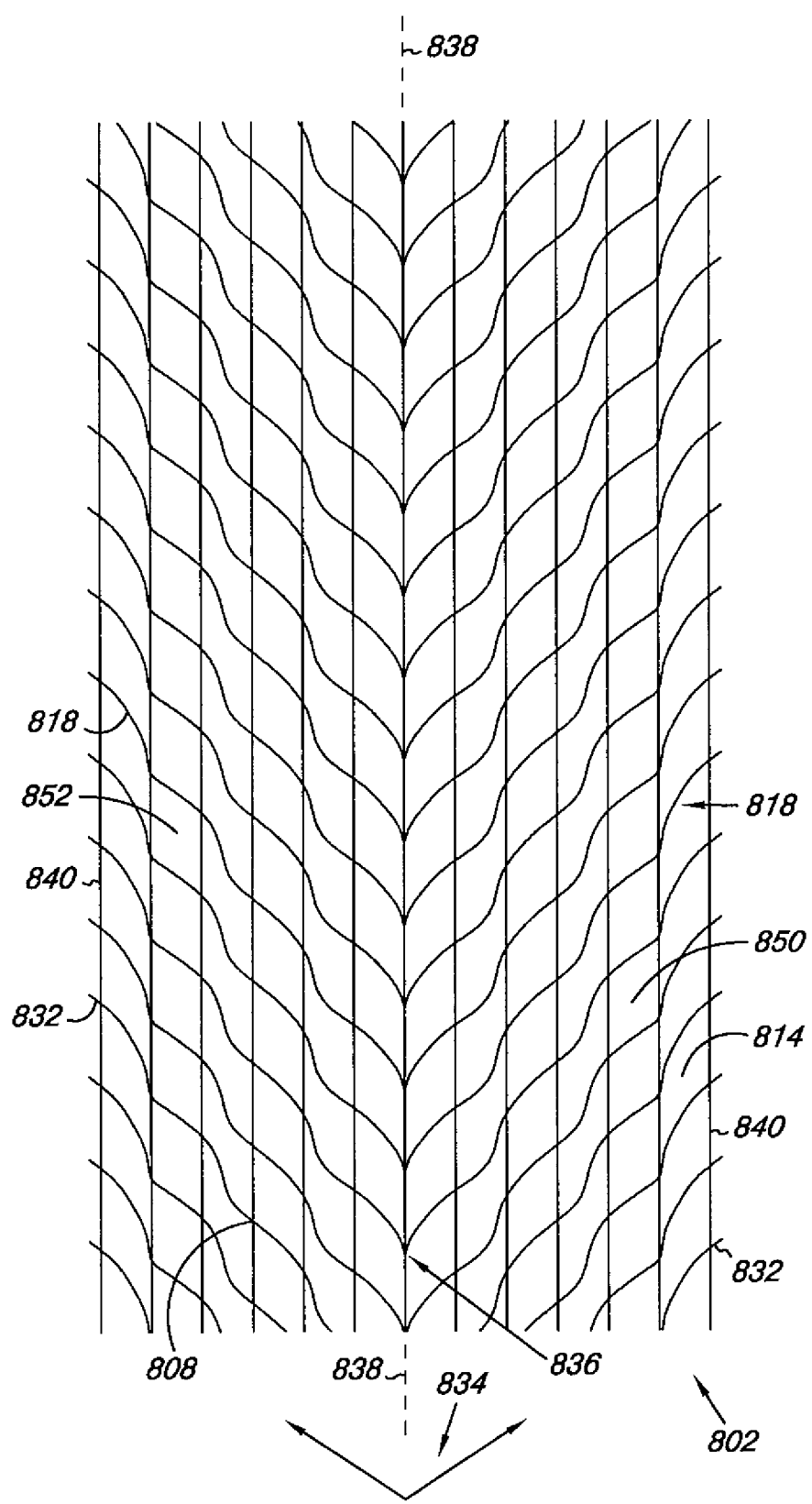
FIG. 8 illustrates an example of a continuous metal sheet of the composite biomaterial according to the present disclosure.

FIG. 8 provides an illustration of an additional continuous metal sheet 802 use in the composite biomaterial according to the present disclosure. As illustrated, the continuous metal sheet 802 includes a first set of members 832 that extend in a radiating pattern 834 from the corner 836 of each of the members 832.

For the various embodiments, the corner 836 of each of the first set of members 832 can be aligned along a center axis 838. In one embodiment, the radiating pattern 834 of the members 832 aligned along the center axis provides a chevron pattern to the members 832. The continuous metal sheet 802 also includes second set of members 840 that extend to intersect the first set of members 832 at junctions 808. In one embodiment, the center axis 838 provides an axis of symmetry for the first set of members 832 and the second set of members 840.

As illustrated, the first set of members 832 include a series of repeating single arcs 818 that change their direction of curvature at each junction 808. For the present embodiment, the second set of members 840 has a linear shape. In an alternative embodiment, the arc of the members could curve in the same direction at each junction, where the direction on one side of the center axis is opposite of the direction on the other side of the center axis. As discussed herein, different combinations of linear and arcuate shaped members could also be used for the continuous metal sheet to provide the radiating pattern generally illustrated in FIGS. 7 and 8. Changes to these patterns and directions of arcs for the members can change the mechanical properties of the composite biomaterial.

As illustrated, the continuous metal sheet 802 includes apertures 814 defined by the members 832 and 840 that have at least two different shapes. In FIG. 8, the members 832 and 840 define a first cell 850 and a second cell 852 that have shapes that are mirror images of each other. In addition, the first and second cells 850, 852 are chiral (i.e., not superimposable on each other). As will be appreciated, other combinations of linear and arcuate shaped members could be used to generate other patterns for the first and second cells that are both mirror images of each other and have chirality.

For the various embodiments, total area of each cell can have a predetermined value of 0.00015 to 0.40 square centimeters. For example, the total area of each cell illustrated in FIG. 3 can be 0.0031 square centimeters. In other examples, the total area of each cell illustrated in FIG. 4 can be 0.0043 square centimeters and the total area of each cell illustrated in FIG. 5 can be 0.017 square centimeters.

For the various embodiments, there can be a number of different relative dimensions for different portions of the members of the continuous metal sheet. For example, the members can have a width and thickness of less than 0.002 inches and that the length to be at least 10 times the width or thickness and that the width is less than or equal to the thickness. In an additional embodiment, the members can have a width and thickness of less than 0.0015 inches and that the length to be at least 20 times the width or thickness and that width is less than or equal to the thickness. These relative ratios of thickness and width of the arcuate can have a profound effect on flexibility of the members and the continuous metal sheet.

In addition, the cells of the continuous metal sheet illustrated herein have an open area (i.e., the apertures) that is a significant percentage of the surface area of the continuous metal sheet. For example, the embodiments of the apertures illustrated in FIGS. 1-8 can have an open area that is from 78 percent to 91 percent of a total area of the cell defined by the arcuate members and junctions. In an alternative embodiment, the open area of the cells can be seventy (70) percent to ninety eight (98) percent of the total area of the cell defined by the arcuate members and junctions. In another embodiment, the open area of the cells can be eighty five (85) percent to ninety five (95) percent of the total area of the cell defined by the arcuate members and junctions.

In addition, the composite biomaterial of the present disclosure can include some additional mechanical features that are useful for the variety of applications discussed herein. For example, the continuous metal sheet of the composite biomaterial can provide a Poisson's ratio having a negative value (i.e., an auxetic). In other words, as the composite biomaterial of the present disclosure is stretched in one direction, it gets wider in the perpendicular direction.

By way of example, the embodiment illustrated in FIGS. 1 and 2 can have negative Poisson ratios. In an additional embodiment, the embodiments illustrated in FIGS. 3 and 4 can have Poisson ratios of approximately zero (0), depending upon the dimensions and loading direction imposed on the composite biomaterial.

For the various embodiments, the aspect ratios of the fenestration patterns discussed herein can also be used to adjust the Poisson's ratio of the composite biomaterial. In an additional embodiment, the continuous metal sheet of the composite biomaterial can provide a Poisson's ratio that is 0.5 or greater.

As discussed herein, the composite biomaterial of the present disclosure can be used in a number of different applications. For example, the composite biomaterial can be used in forming a valve leaflet for use in a prosthetic valve (e.g., cardiac valve and/or venous valve). Natural valve leaflets are anisotropic in complex ways that vary over the surface of the structure. For example, natural valve leaflets exhibit differing degrees of stiffness and elasticity depending on the location in the leaflet. In natural valve leaflets, collagen fibers reinforce the valve tissue and provide the requisite structural integrity. Natural heart valve leaflet tissue is a composite material that includes collagen fibers in bundles, which are arranged in a special structure and orientation, which provide a desired mechanical behavior by accommodating the principal stresses in the leaflet because the orientation of collagen bundles coincides with these stresses.

The composite biomaterial of the present disclosure can be used to mimic the mechanical behavior of the natural valve leaflet. As illustrated herein, the selection and combination of the continuous metal sheet having at least one of the fenestration patterns and the polymer layer can be used to tailor the valve leaflet to provide an even stress distribution across the valve leaflet. In addition, the composite biomaterials of the present disclosure can be tailored to handle the high dynamic tensile and bending stresses while minimizing bending and wrinkling of the leaflet during the valve opening and closing.

Figure 9:
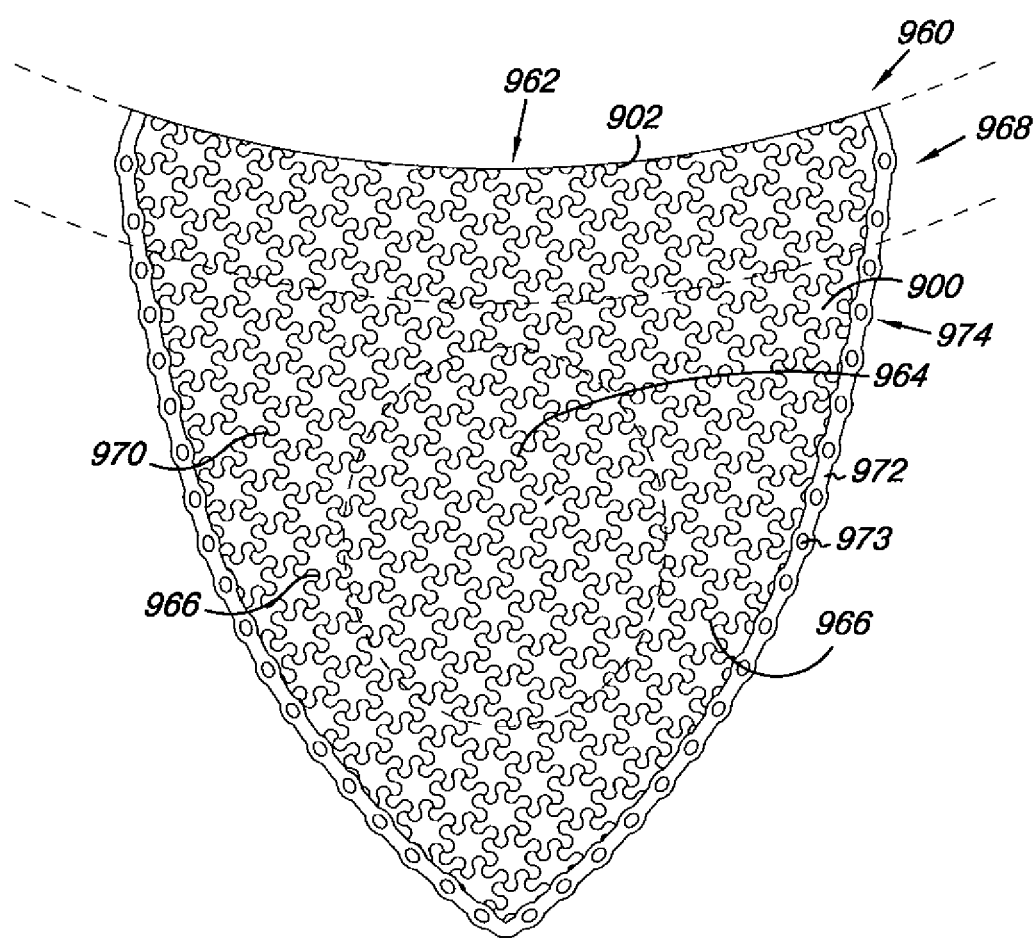
FIG. 9 illustrates an example of a valve leaflet formed from an embodiment of the composite biomaterial according to the present disclosure.

FIG. 9 provides an illustration of a valve leaflet 960 formed with the composite biomaterial 900 of the present disclosure. In one embodiment, the valve leaflet 960 includes a commissure region 962, a leaflet body region 964, a strain relief region 966, and a coaptation region 968. In one embodiment, these regions 962, 964, 966 and 968 can include one or more fenestration patterns configured in such a manner as to tailor the mechanical characteristics of the leaflet 960 to mimic the complex characteristics to native valve leaflets.

In one embodiment, different fenestration patterns, as discussed herein, can be used for one or more of the regions 962, 964, 966 and/or 968 so as to provide specific desired behaviors to the different regions of the composite biomaterial. For example, the continuous metal sheet 902 of composite biomaterial 900 can have a first fenestration pattern 968 with a first compliance in one or more of the regions (e.g., the commissure region 962), and a second fenestration pattern 970, or same pattern but different dimensions (strut width, thickness, or pattern cell size), having a compliance that is different than the compliance of the first fenestration pattern in one or more of the other regions (e.g., the coaptation region 968) of the valve leaflet 960. As will be appreciated, more than two fenestration patterns can be used in the composite biomaterial 900 of the valve leaflet 960.

The valve leaflet 960 can also include a border strip 972. In one embodiment, the border strip 972 defines at least a portion of a perimeter 974 of the composite biomaterial 900. In one embodiment, the border strip 972 and the fenestration patterns are formed from the continuous metal sheet 902. The border strip 972 may be connected to the fenestrated portion of the continuous metal sheet 902 with a series of flexible members that will allow or enhance the ability of the composite biomaterial 900 to flex.

The border strip 972 can also have a configuration that is different than the one or more fenestration patterns of the composite biomaterial 900. For example, as illustrated in FIG. 9 the border strip 972 is a narrow piece of the continuous metal sheet 902 having openings 973 to receive fasteners to secure the valve leaflet 960 to a cardiac valve frame. Examples of fasteners for securing the valve leaflet 960 to a valve frame can include rivets and/or sutures. Other types of fasteners or bonding mechanisms (e.g., staples, adhesives and or welding) could also be used.

Figure 10:
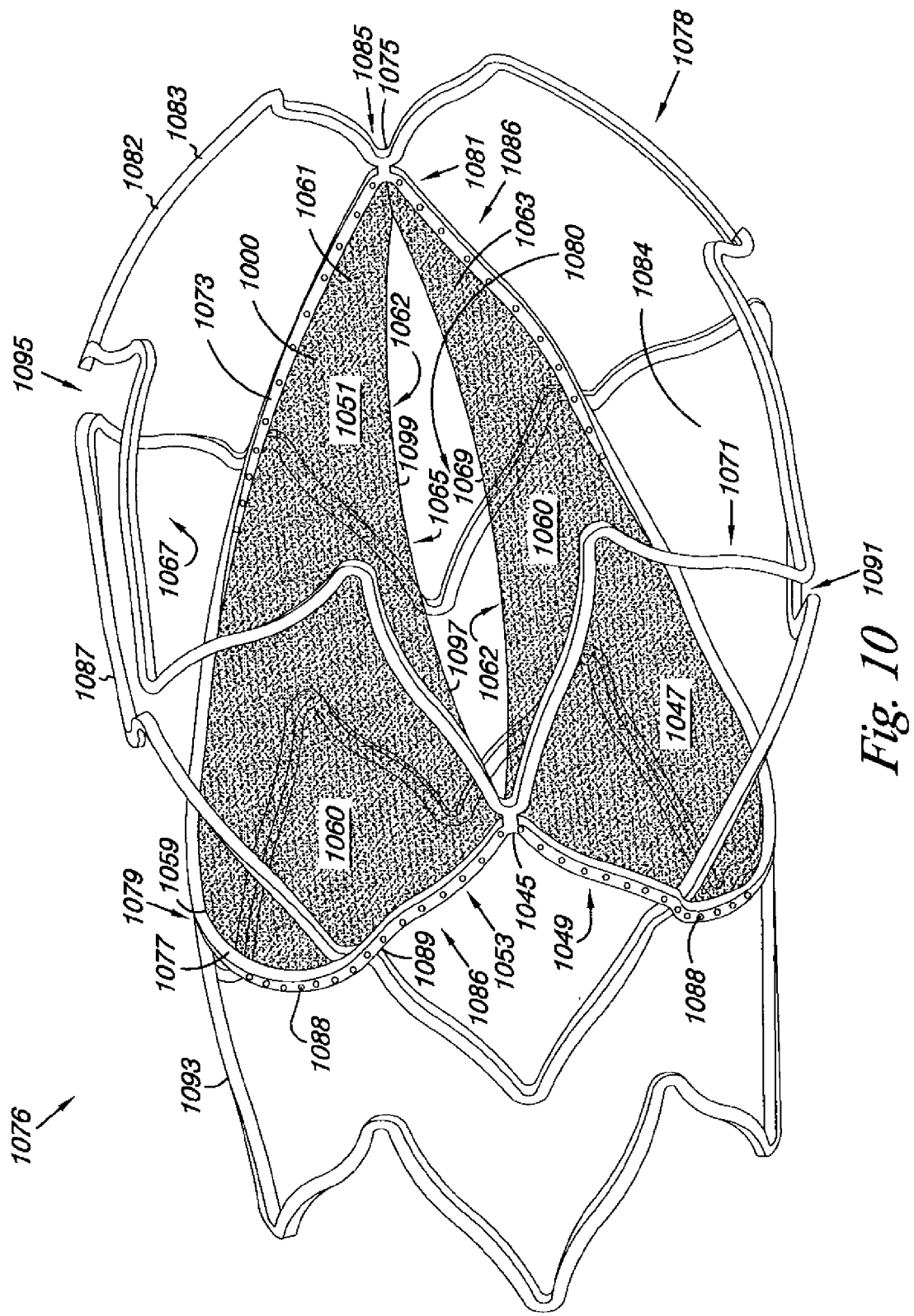
FIG. 10 illustrates an example of a prosthetic valve having valve leaflets formed from an embodiment of the composite biomaterial according to the present disclosure.

FIG. 10 illustrates an embodiment of a valve 1076. Embodiments of the valve 1076 include a valve frame 1078 and valve leaflets 1060 that can be implanted through minimally-invasive techniques into a body lumen. In one example, embodiments of the valve 1076 may help to maintain antegrade blood flow, while decreasing retrograde blood flow in a venous system of individuals having venous insufficiency, such as venous insufficiency in the legs. In another example, embodiments of the valve can be used to replace and/or augment an aortic valve. Use of the valve embodiments can also be possible in other portions of the vasculature.

The valve 1076 shown in FIG. 10 can be implanted within a fluid passageway of a body lumen, such as for replacement and/or augmentation of a valve structure within the body lumen (e.g., a venous valve). In some embodiments, the valve 1076 of the present disclosure may be beneficial to regulate the flow of a bodily fluid through the body lumen in a single direction.

As shown, the valve 1076 includes valve leaflets 1060 having surfaces defining a reversibly sealable opening for unidirectional flow of a liquid through the valve 1076. For the present embodiment, the valve 1076 includes two valve leaflets 1060 for a bi-leaflet configuration. As appreciated, mono-leaflet, tri-leaflet and/or multi-leaflet configurations are also possible. In addition, although the embodiment of a bi-leaflet configuration is used to explain the valve 1076, one skilled in the art will appreciate that the same can be applied to other leaflet configurations.

The valve 1076 includes a valve frame 1078 with the valve leaflets 1060 attached to the valve frame 1078. The valve leaflets 1060 can repeatedly move between an open state and a closed state for unidirectional flow of a liquid through a lumen 1080 of the valve 1076.

In some embodiments, the valve 1076 can have a unitary structure with an open frame configuration. For example, the open frame configuration can include frame members 1082 that define openings 1084 across the valve frame 1078 through which valve leaflets 1060 formed with, for example, the composite biomaterial 1000 of the present disclosure, can radially-collapse and radially-expand to provide unidirectional flow through the valve 1076. The valve 1076 can also include valve leaflets 1060 formed of other materials, as discussed further herein.

As shown in FIG. 10, the fluid flows through the valve 1076 in an upward direction. As such, as shown in FIG. 10, the bottom of the valve 1076 is "distal" and the top of the valve 1076 is "proximal." The valve frame 1078 includes a first frame member 1077 including a leaflet connection region 1086. A distal end 1079 of the first frame member 1077 defines a distal cross-sectional area and a proximal end 1081 of the first frame member 1077 defines a proximal cross-sectional area. As shown, the proximal cross-sectional area is larger than the distal cross-sectional area, as discussed further herein.

The valve frame 1078 also includes a second frame member 1083 having a distal end 1085 connected to the proximal end 1081 of the first frame member 1077. In some embodiments, the second frame member 1083 can be connected to the proximal end 1081 of the first frame member 1077 and extend in a proximal direction, such that the second frame member 1083 increases the length of the valve 1076.

As illustrated in FIG. 10, the distal end 1085 of the second frame member 1083 and the proximal end 1081 of the first frame member 1077 define a circular proximal cross-sectional area. As used herein, a "circular" cross-sectional area refers to the general shape the body lumen forms once the valve 1076 is implanted at a treatment site. For example, a generally tubular valve frame consisting of four frame members longitudinally extending from a proximal end to a distal end would cause a body lumen to form a square shape once the valve frame is implanted at the treatment site. In embodiments of the present disclosure, however, the distal end 1085 of the second frame member 1083 and the proximal end 1081 of the first frame member 1077 define a circular proximal cross-sectional area due to the configuration of the first and second frame members 1077, 1083. More specifically, the distal end 1085 of the second frame member 1083 and the proximal end 1081 of the first frame member 1077 provide enough support to ensure that the body lumen will form a circular shape when the valve is implanted in the treatment site. Other cross-sectional shapes are also possible, including, but not limited to, oval or elliptical.

The valve frame 1078 also includes a third frame member 1087 connected to a middle portion 1089 of the first frame member 1077. In some embodiments, the third frame member 1087 can extend from the middle portion 1089 of the first frame member 1077 in a proximal direction. A proximal end 1091 of the third frame member 1087 defines a circular proximal cross-sectional area approximately equal to the circular proximal cross-sectional area defined by the distal end 1085 of the second frame member 1083 and the proximal end 1081 of the first frame member 1077.

As illustrated in FIG. 10, the valve frame 1078 can also include a fourth frame member 1093. The fourth frame member 1093 can be connected to the distal end 1079 of the first frame member 1077 and can define a fourth circular cross-sectional area. In some embodiments, the fourth circular cross-sectional area can be approximately equal to the distal cross-sectional area of the first frame member 1077. The fourth frame member 1093 can serve as an additional structural member to anchor the valve frame 1078 at a treatment site. However, in embodiments where there is a limited amount of space for the valve 1076 (e.g., aortic valve replacement), the fourth frame member 1093 may not be included, or may be modified to take up less area as compared to that shown in FIG. 10.

It is important to note that although the current valve 1076 description discusses four frame members, it is also possible to have more members over the same valve frame 1078 length. The purpose of the frame members are to anchor the valve 1076 and prevent intrusion of either the native defective valve and/or vein wall into the interior of the valve frame 1078, thereby preventing contact with the valve leaflets 1060. However, the use of additional frame members must be balanced with the desire to minimize the use of additional frame members to prevent adverse healing response. To help minimize the effects of additional frame members, the additional frame members can be shorter in length and can have a narrow strut width. The modification to the additional frame members can also help allow the valve 1076 to be loaded into a delivery catheter.

As illustrated in FIG. 10, the proximal end 1091 of the third frame member 1087, the distal end 1085 of the second frame member 1083, and the proximal end 1081 of the first frame member 1077 form a bulbous portion 1095 around the leaflet connection region 1086 of the first frame member 1077. As illustrated, the proximal end 1091 of the third frame member 1087, the distal end 1085 of the second frame member 1083, and the proximal end 1081 of the first frame member 1077 extend radially from the distal end 1079 of the first frame member 1077 to define the bulbous portion 1095. More specifically, the bulbous portion 1095 can begin at the distal end 1079 of the first frame member 1077 and can reach a maximum cross-sectional area at the proximal end 1081 of the first frame member 1077. From the proximal end 1081 of the first frame member 1077, the bulbous portion 1095 can taper to a smaller cross-sectional area at the most-proximal end of the second frame member 1083. In some embodiments, the smaller cross-sectional area at the most-proximal end of the second frame member 1083 can be approximately equal to the circular cross-sectional area defined by the distal end 1079 of the first frame member 1077.

In some embodiments, the proximal end 1081 of the first frame member 1077 can be radially expanded in order to define the proximal cross-sectional area and form the bulbous portion 1095. Similarly, the distal end 1085 of the second frame member 1083 and the proximal end 1091 of the third frame member 1087 can be radially expanded to define the circular distal cross-sectional area and the circular proximal cross-sectional area, respectively.

In some embodiments, the perimeter of the bulbous portion 1095 can have a round shape. Other shapes of the bulbous portion are also possible, including, but not limited to, one or more of a spherical, semi-spherical, ovoid, semi-ovoid, conical, semi-conical, torus, semi-torus, cylindrical, and semi-cylindrical. In addition, in one embodiment, the bulbous portions 1095 can be formed such that the bulbous portions 1095 on each side of the valve leaflets 1060 are equivalent to each other (i.e., mirror images). In addition, each of the two or more bulbous portions 1095 can have different shapes, as discussed herein. In other words, the bulbous portion 1095 need not have the same shape as the other bulbous portion 1095 of the valve frame 1078.

In addition, the proximal end 1091 of the third frame member 1087, the distal end 1085 of the second frame member 1083, and the proximal end 1081 of the first frame member 1077 can move radially as the valve 1076 radially collapses and expands. In the various embodiments described herein, the frame members forming the bulbous portion 1095 can provide a spring force (e.g., elastic potential energy) to counter radial compression of the valve frame 1078 towards its uncompressed state.

Also, the compressible nature of the valve frame 1078 can accommodate changes in body lumen size (e.g., diameter of the body lumen) by flexing to expand and/or contract to change the diameter of the valve frame 1078. The valve frame 1078 can also provide sufficient contact and expansion force with the surface of a body lumen wall to encourage fixation of the valve 1076 and to prevent retrograde flow within the body lumen around the edges of the valve frame 1078, for example, the leaflet connection region 1086, and the surface of a lumen when combined with a closed state of the valve leaflets 1060 attached thereto. Anchoring elements (e.g., barbs) can also be included with the valve frame 1078.

The frame members 1082 can have similar and/or different cross-sectional geometries and/or cross-sectional dimensions along their length. The similarity and/or the differences in the cross-sectional geometries and/or cross-sectional dimensions can be based on one or more desired functions to be elicited from each portion of the valve frame 1078. For example, the first frame member 1077 and the second frame member 1083 can have a similar cross-sectional geometry along their length. Examples of cross-sectional geometries include, but are not limited to, round (e.g., circular, oval, and/or elliptical), rectangular geometries having perpendicular sides, one or more convex sides, or one or more concave sides; semi-circular, triangular, tubular, I-shaped, T-shaped, parallelogram-shaped, and/or trapezoidal.

Alternatively, the cross-sectional dimensions of one or more geometries of the frame members 1082 can change from one portion of the valve frame 1078 to another portion of the valve frame 1078. For example, portions of the first frame member 1077 can taper (i.e., transition) from a first geometric dimension to a second geometric dimension different than the first geometric dimension. These embodiments, however, are not limited to the present examples, as other cross-sectional geometries and dimensions are also possible. As such, the present disclosure should not be limited to the frames provided in the illustration herein.

As illustrated, the valve frame 1078 includes a leaflet connection region 1086 along the first frame member 1077. The leaflet connection region 1086 extends from the proximal end 1081 to the distal end 1079 in order to ensure that retrograde fluid flow is prevented from leaking around the valve frame 1078.

As shown in FIG. 10, the valve leaflets 1060 include a first valve leaflet 1061 and a second valve leaflet 1063. As illustrated, the first and second valve leaflets 1061, 1063 are connected to the valve leaflet connection region 1086. The first and second valve leaflet 1061, 1063 have surfaces that define a commissure region 1062 that reversibly opens and closes for unidirectional flow of a liquid through the valve 1076. As used herein, the commissure region 1062 includes portions of the valve leaflet 1060 surfaces that reversibly form a connection to allow fluid to flow through the valve 1076 in essentially one direction. For example, the first valve leaflet 1061 can include a first inflow surface 1053 and a first outflow surface 1051 opposite the first inflow surface 1053. Similarly, the second valve leaflet 1063 can include a second inflow surface 1049 and a second outflow surface 1047 opposite the second inflow surface 1049. The first and second valve leaflets 1061, 1063 can move between a closed position in which fluid flow through the lumen 1080 can be restricted and an open position in which fluid flow through the lumen 1080 is permitted. As such, the commissure region 1062 can include portions of the first and second inflow surfaces 1053, 1049 that form a connection when the valve leaflets 1060 are in the closed position.

As will be appreciated by one skilled in the art, the valve 1076 can also include a third valve leaflet, or a third valve leaflet and a fourth valve leaflet. In such embodiments, the valve leaflets 1060 can be set along the first frame member 1077 such that the valve leaflets 1060 can move between a closed position in which fluid flow through the lumen 1080 can be restricted and an open position in which fluid flow through the lumen 1080 is permitted. The valve leaflets 1060 can be identical in size, shape, and material, or the valve leaflets 1060 can be formed of different materials and be of varying sizes.

In the present example, the valve leaflets 1060 can be coupled, as described more fully herein, to at least the valve leaflet connection region 1086. As illustrated, the valve leaflets 1060 include a region 1065 of the valve leaflets 1061, 1063 that can move relative the valve frame 1078. The region 1065 of the valve leaflets 1060 can be unbound (i.e., unsupported) by the valve frame 1078 and extends between the proximal end 1081 of the first frame member 1077 to allow the commissure region 1062 to reversibly open and close for unidirectional flow of the liquid through the valve 1076.

In an additional embodiment, the valve leaflets 1060 in their open configuration can have a circumference that is less than the circumference of the valve frame 1078. For example, as illustrated, the valve leaflets 1060 in their open position include a gap 1067 between a free edge 1069 of each valve leaflet 1060 and the bulbous portion 1095 of the valve frame 1078.

In some embodiments, the first and second valve leaflets 1061, 1063 and the bulbous portion 1095 of the valve frame 1078 provide surfaces that define a sinus 1071. As illustrated, the sinus 1071 provides a dilated channel or receptacle defined by a volume between the first and second outflow surfaces 1051, 1047 of the first valve and second valve leaflets 1061, 1063 in the open position and the circular proximal cross-sectional area defined by the distal end 1085 of the second frame member 1083 and the proximal end 1081 of the first frame member 1077.

In some embodiments, the presence of the sinus 1071 better ensures that the valve leaflets 1060 do not come into contact with a significant portion of the valve frame 1078 and/or the inner wall of the vessel in which the valve 1076 is implanted. For example, the sinus 1071 can help prevent adhesion between the valve leaflets 1060 and the vessel wall due to the presence of a recirculation volume of blood there between.

The sinus 1071 can also allow for improved valve leaflet 1060 dynamics (e.g., opening and closing of the valve leaflets 1060). For example, the sinus 1071 can allow for pressure differentials across the surfaces of the valve leaflets 1060 that provide for more rapid closing of the valve leaflets 1060 as the retrograde blood flow begins, as will be discussed herein.

In addition, as the leaflets 1060 are not in contact with the vessel wall (i.e., except at the leaflet connection region 1086) and/or the bulbous portion 1095 of the valve frame 1078, the leaflets 1060 can be more responsive to changes in the flow direction. The presence of the sinus 1071 allows slower moving fluid (e.g., blood) to move into the sinus 1071 and faster moving blood on the flow side of the leaflets 1060 to create a pressure differential. This pressure differential across the valve leaflets 1060 provides for a Bernoulli effect for which an increase in fluid flow velocity there occurs simultaneously with a decrease in pressure. So as fluid flow becomes retrograde the fluid velocity through the opening of the valve leaflets 1060 is larger than the fluid flow in the sinus 1071. As a result there is a lower pressure in the opening of the valve leaflets 1060 that causes the opening to close more quickly and be more responsive to small changes in reversal of flow as compared to valves without the sinus 1071.

In various embodiments, the configuration of the present embodiments allows the leaflets 1060 to experience a low shear as compared to angled leaflets which are subject to high shear and direct impact with flowing blood. This can be attributed to the alignment of the valve leaflets 1060, the first frame member 1077, and the adjacent vein segment, above and below the sinus 1071. The sinus 1071 also allows for recirculation of blood within the sinus 1071 that can clean out potential thrombus buildup in the bottom of the sinus 1071.

As discussed herein, in some embodiments, under antegrade fluid flow (i.e., positive fluid pressure) from the distal end 1079 of the first frame member 1077 towards the proximal end 1081 of the first frame member 1077, the valve leaflets 1060 can expand toward an inner surface of the bulbous portion 1095 of the valve frame 1078 to create an opening through which fluid is permitted to move. In such embodiments, the valve leaflets 1060 can expand to define a semitubular structure having a circular cross-section when fluid opens the commissure region 1062.

In some embodiments, the dimensions and configuration of the valve leaflets 1060 can include proportional relationships to structures of the valve frame 1078. For example, the first and second valve leaflets 1061, 1063 can each have a predetermined length between the proximal ends 1081 of the first frame member 1077. Specifically, as illustrated in FIG. 10, the distance from a first distal end point 1045 to a second proximal end point 1075 can define a first length of the first and second valve leaflets 1061, 1063. In addition, the free edge 1069 of the first and second valve leaflets 1061, 1063 can define a curve 1097 with a bottom 1099, where the bottom 1099 is the nadir of the curve 1097. The second length of the first and second leaflets 1061, 1063 can be defined as the distance between the bottom 1099 of the curve 1097 and the most distal point 1059 at the distal end 1079 of the first frame member 1077. In some embodiments, the ratio of the first length to the second length can be 1:1.5. In various embodiments, the ratio of the first length to the second length can be 1:1.

The embodiments of the valve frame described herein can be constructed of one or more of a number of materials and in a variety of configurations. The valve frame embodiments can have a unitary structure with an open frame configuration. The valve frame can also be self-expanding. Examples of self-expanding valve frames include those formed from temperature-sensitive memory alloy which changes shape at a designated temperature or temperature range, such as Nitinol. Alternatively, the self-expanding valve frames can include those having a spring-bias. In addition, the valve frame 1078 can have a configuration that allows the frame embodiments to be radially expandable through the use of a balloon catheter. In such embodiments, the valve frame 1078 can be provided in separate pieces (e.g., two frame pieces) that are delivered individually to the implant site.

The embodiments of the valve frame 1078 can also be formed from one or more contiguous frame members. For example, the first and second frame members 1077, 1083 of the valve frame 1078 can be formed from a single contiguous member. The single contiguous member can be bent around an elongate tubular mandrel to form the valve frame. The free ends of the single contiguous member can then be welded, fused, crimped, or otherwise joined together to form the valve frame. In an additional embodiment, the first and second frame members 1077, 1083 of the valve frame 1078 can be derived (e.g., laser cut, water cut) from a single tubular segment. Similar approaches can be used with respect to the third frame member 1087 and the fourth frame member 1093. In an alternative embodiment, methods of joining the frame members 1082 of the valve frame 1078 to create an elastic region include, but are not limited to, welding, gluing, and fusing the frame members 1082. The valve frame 1078 can be heat set by a method as is typically known for the material which forms the valve frame 1078.

The valve frame 1078 can be formed from a number of materials. For example, the valve frame 1078 can be formed from a biocompatible metal, metal alloy, polymeric material, or combination thereof. As described herein, the valve frame 1078 can be self-expanding or balloon expandable. In addition, the valve frame 1078 can be configured so as to have the ability to move radially between the collapsed state and the expanded state. Examples of suitable materials include, but are not limited to, medical grade stainless steel (e.g., 316L), titanium, tantalum, platinum alloys, niobium alloys, cobalt alloys, alginate, or combinations thereof. Additional valve frame 1078 embodiments may be formed from a shape-memory material, such as shape memory plastics, polymers, and thermoplastic materials. Shaped memory alloys having superelastic properties generally made from ratios of nickel and titanium, commonly known as Nitinol, are also possible materials. Other materials are also possible.

In addition, the lumen 1080 can include a number of sizes. For example, the size of the lumen 1080 can be determined based upon the type of body lumen and the body lumen size in which the valve is to be placed. In an additional example, there can also be a minimum value for the width for the valve frame 1078 that ensures that the valve frame 1078 will have an appropriate expansion force against the inner wall of the body lumen in which the valve 1076 is being placed.

The valve 1076 can further include one or more radiopaque markers (e.g., rivets, tabs, sleeves, welds). For example, one or more portions of the frame can be formed from a radiopaque material. Radiopaque markers can be attached to, electroplated, dipped, and/or coated onto one or more locations along the valve frame 1078. Examples of radiopaque material include, but are not limited to, gold, tantalum, and platinum.

The position of the one or more radiopaque markers can be selected so as to provide information on the position, location, and orientation (e.g., axial, directional, and/or clocking position) of the valve 1076 during its implantation. For example, radiopaque markers can be configured radially and longitudinally (e.g., around and along portions of the first frame member 1077) on predetermined portions of the valve frame 1078 to allow the radial and axial position of the valve frame 1078 to be determined. So, in one embodiment a radiograph image of the valve frame 1078 taken parallel to the commissural plane (e.g., defined by a plane passing through the first and second proximal end points 1045, 1075 of the first frame member 1077 and a point along the center axis proximal or distal to this plane) of the valve leaflets 1060 in a first clock position can produce a first predetermined radiograph image (e.g., an imaging having the appearance of an inverted "V") and a radiographic image taken perpendicular to the commissural plane in a second clock position can produce a second predetermined radiograph image (e.g., an imaging having the appearance of an upright "U") distinguishable from the first predetermined radiograph image.

In some embodiments, the first and second predetermined radiograph images allow the radial position of the valve leaflets 1060 to be better identified within the vessel. This then allows a clocking position for the valve 1076 to be determined so that the valve 1076 can be positioned in a more natural orientation relative the compressive forces the valve 1076 will experience in situ. In other words, determining the clocking of the valve 1076, as described herein, allows the valve 1076 to be radially positioned in a same orientation as a native valve that it is replacing and/or augmenting.

In some embodiments, the material of the valve leaflets 1060 can be sufficiently thin and pliable so as to permit radially-collapsing of the valve leaflets 1060 for delivery by catheter to a location within a body lumen. The valve leaflets 1060 can be constructed of a fluid-impermeable biocompatible material that can be either synthetic or biologic. Possible synthetic materials include, but are not limited to, expanded polytetrafluoroethylene (ePTFE), polytetrafluoroethylene (PTFE), polystyrene-polyisobutylene-polystyrene (SIBS), polyurethane, segmented poly(carbonate-urethane), Dacron, polyethlylene (PE), polyethylene terephthalate (PET), silk, Rayon, Silicone, or the like. Composites of synthetic materials are also possible. Possible biologic materials include, but are not limited to, autologous, allogeneic or xenograft material. These include explanted veins and decellularized basement membrane materials (such as non-crosslinked bladder membrane or amnionic membrane), such as small intestine submucosa (SIS) or umbilical vein. As will be appreciated, blends or mixtures of two or more of the materials provided herein are possible. For example, SIBS can be blended with one or more basement membrane materials.

In addition, in one embodiment, the valve leaflets 1060 can be constructed of a semi-permeable biocompatible material formed of an ePTFE/Nickel-Titanium mesh. In this embodiment, the composite valve leaflets 1060 can be initially semi-permeable to blood until the mesh is filled with fibrin, red blood cells, and platelets from the blood, making the composite valve leaflets 1060 fluid-impermeable.

In addition, valve leaflets 1060 formed of the composite biomaterial, as described herein, can be used with the valve 1076. For example, the border strip of the valve leaflet 1060 can be attached to the valve frame 1078. In some embodiments, the valve leaflet 1060 can be attached to the leaflet connection region 1086 through the use of rivets 1088. In various embodiment, the rivets 1088 are from the material of the valve frame 1078. Alternatively, the rivets can be separate elements that are secured across the openings 1073 of the border strip 1072 and opening through the frame member 1082.

In some embodiments, the rivets can be formed of, or coated with a radiopaque material (e.g., gold, tantalum, and platinum) that would allow for visualization of the position, location, and orientation (e.g., axial, directional, and/or clocking position) of the valve 1076 during its implantation.

As described herein, a number of additional methods exist for attaching the valve leaflets 1060 to the valve frame 1078. For example, the valve leaflets 1060 can be secured to the first frame member 1077 at the leaflet connection region 1086 through the use of biocompatible staples, glues, sutures or combinations thereof. In additional embodiments, the valve leaflets 1060 can be coupled to the first frame member 1077 through the use of heat sealing, solvent bonding, adhesive bonding, or welding the valve leaflets 1060 to the valve frame 1078.

The valve leaflets 1060 can have a variety of sizes and shapes. For example, each of the valve leaflets 1060 can have a similar size and shape. Alternatively, each of the valve leaflets 1060 need not have a similar size and shape (i.e., the valve leaflets can have a different size and shape with respect to each other).

In additional embodiments, the valve leaflets 1060 can include one or more support structures, where the support structures can be integrated into and/or onto the valve leaflets 1060. For example, the valve leaflets 1060 can include one or more support ribs having a predetermined shape. In some embodiments, the predetermined shape of the support ribs can include a curved bias so as to provide the valve leaflets 1060 with a curved configuration. Support ribs can be constructed of a flexible material and have dimensions (e.g., thickness, width and length) and cross-sectional shape that allows the support ribs to be flexible when the valve leaflets 1060 are urged into an open position, and stiff when the valve leaflets 1060 are urged into a closed position upon experiencing sufficient back flow pressure from the direction downstream from the valve 1076. In an additional embodiment, support ribs can also be attached to valve frame 1078 so as to impart a spring bias to the valve leaflets 1060 in either the open or the closed position.

The valve leaflets 1060 to be used with the valve frame 1078 of the present disclosure may also be treated and/or coated with any number of surface or material treatments. For example, the valve leaflets 1060 can be treated with one or more biologically active compounds and/or materials that may promote and/or inhibit endothelization and/or smooth muscle cell growth of the valve leaflets 1060. Similarly, the valve leaflets 1060 may be seeded and covered with cultured tissue cells (e.g., endothelial cells) derived from a either a donor or the host patient which are attached to the valve leaflets 1060. The cultured tissue cells may be initially positioned to extend either partially or fully over the valve leaflets 1060.

Valve leaflets 1060 can also be capable of inhibiting thrombus formation. Additionally, valve leaflets 1060 may either prevent or facilitate tissue ingrowth there through, as the particular application for the valve 1076 may dictate. For example, valve leaflets 1060 on the outer surfaces 1051, 1047 may be formed from a porous material to facilitate tissue ingrowth there through, while valve leaflets 1060 on the inner surfaces 1053, 1049 may be formed from a material or a treated material which inhibits tissue ingrowth.

Additional embodiments of a valve to be used with the synthetic composite material of the present disclosure are also provided in co-pending U.S. patent application Ser. No. 11/150,331 filed (DKT# 04-0081US) filed Jun. 10, 2005 and entitled "Venous Valve, System, and Method," which is incorporated herein by reference in its entirety.

With regard to the synthetic composite material, as discussed herein, the fenestration pattern of the continuous metal sheet can include a repeated series of the apertures having two or more different shapes, where each of the two or more shapes either has or does not have the same surface area. In other words, the fenestration pattern can continuously change across the surface of the continuous metal sheet (i.e., along a line of symmetry no two fenestrations are alike).

In one embodiment, this continuous change in fenestration pattern helps to avoid possibilities of discontinuities, as discussed above, in the composite biomaterial. For the various embodiments, the continuous change in fenestration pattern can also help to even out the stresses even across the surface of the composite biomaterial when used, for example, as a leaflet for a valve. By better distributing the stresses across the surface of the composite biomaterial the curvature of the composite biomaterial can change smoothly (i.e., does not have discontinuities).

FIGS. 11-13 provide illustrations of such heterogeneous fenestration patterns 1116, 1216 and 1316. As illustrated, the fenestration patterns 1116, 1216 and 1316 have an initial fenestration pattern 1190, 1290 and 1390 generally along a central region 1192, 1292 and 1392 of the leaflet body region 1164, 1264 and 1364. The initial fenestration pattern 1190, 1290 and 1390 changes shape as the continuous metal sheet 1102, 1202, and 1302 extends towards the boarder strip 1172, 1272, and 1372; coaptation region 1168, 1268, and 1368; and the commissure region 1162, 1262, and 1362.

The change in shape of the initial fenestration pattern 1190, 1290 and 1390 can, in one embodiment, be symmetrical relative the central region 1192, 1292 and 1392. Alternatively, the change in shape of the initial fenestration pattern 1190, 1290 and 1390 can, in another embodiment, be asymmetrical relative the central region 1192, 1292 and 1392.

The embodiments illustrated in FIGS. 11-12 further illustrate a different pattern for the continuous metal sheet 1102 and 1202 in the coaptation region 1168 and 1268. As illustrated, the fenestration pattern 1116 and 1216 in the coaptation region 1168 and 1268 can provide for an edge of the continuous metal sheet 1102 and 1202 having a serpentine pattern 1194 and 1294. For the various embodiments, the serpentine pattern 1194 and 1294 of the continuous metal sheet 1102 and 1202 provides the coaptation region 1168 and 1268 with greater flexibility as compared to a coaptation region without the serpentine pattern. In addition, the serpentine pattern 1194 and 1294 provide for additional surface area to which the polymer layer 1104 and 1204 can be secured.

For the various embodiments, the amplitude and frequency of the serpentine pattern 1194 and 1294 at the edge of the continuous metal sheet 1102 and 1202 can be dependent upon the fenestration pattern of remainder of continuous metal sheet 1102 and 1202. For example, when the fenestration pattern provides for a relatively flexible continuous metal sheet, the amplitude of the serpentine pattern needs to be relatively high. Similarly, when the fenestration pattern provides for a relatively stiffer continuous metal sheet, the amplitude of the serpentine pattern needs to be relatively small.

The continuous metal sheet 1102, 1202, and 1302 also illustrate embodiments of the strain relief region 1166, 1266, and 1366. As illustrated, the strain relief region 1166, 1266, and 1366 provides a transition region between the boarder strip 1172, 1272, and 1372 and the remainder of the continuous metal sheet 1102, 1202, and 1302. In one embodiment, the strain relief region 1166, 1266, and 1366 has struts that transition from a first thickness, and/or width (shown generally at 1196, 1296 and 1396) to a second thickness, and/or width (shown generally at 1198, 1298 and 1398) that is smaller than the first thickness. So, for example the struts of the continuous metal sheet 1102, 1202, and 1302 in the strain relief region 1166, 1266, and 1366 change size and/or shape as the continuous metal sheet 1102, 1202, and 1302 merges with boarder strip 1172, 1272, and 1372.

A variety of approaches can be taken in forming the valve leaflets of the present disclosure. For example, in one embodiment one or more of the desired fenestration patterns can be formed in the continuous metal sheet, as discussed herein. One or more of the polymer layers can then be applied to the continuous metal sheet to form the composite biomaterial. The composite biomaterial can then be shaped in to a form based on the desired application of the material.

In an additional embodiment features of the composite biomaterial and/or of the object to be formed with the composite biomaterial can be used in forming the object. For example, as illustrated in FIGS. 7 and 8 above, some of the embodiments of the composite biomaterial of the present disclosure have an axis of symmetry. In addition, there are objects that can be formed from composite biomaterial that also have an axis of symmetry. One example is that of the valve leaflet, as discussed herein, where an axis of symmetry can extend from a point that approximately bisects the commissure region down to a low point of the valve leaflet so as to divide the leaflet into lateral halves. In forming the valve leaflet with the composite biomaterial of the present disclosure, the axis of symmetry for the continuous metal sheet illustrated in FIGS. 7 and 8 can be used as the axis of symmetry in forming the valve leaflet from the composite biomaterial.

In alternative embodiment, a strain field can be formed in, or imposed upon, the composite biomaterial discussed herein prior to forming the object (e.g., the valve). In one embodiment, this imposed strain field can be applied to the composite biomaterial to provide a predetermined fenestration pattern in the continuous metal sheet. In one embodiment, the predetermined fenestration pattern formed with the imposed strain field is a different pattern as compared to the starting fenestration pattern of the unstrained continuous metal sheet.

Embodiments of the present disclosure include a composite biomaterial that include a continuous metal sheet having a first set of members that extend in a radiating pattern from a corner, the corner of each of the first set of members being aligned along a center axis, and a second set of members that extend to intersect the first set of members; and a polymer layer over at least one surface of the continuous metal sheet. In various embodiments, the first set of members that extend in a radiating pattern from the corner extend in a chevron pattern. In various embodiments, the first set of members and the second set of members have a linear shape. In various embodiments, the first set of members have an arcuate shape. In various embodiments, the second set of members have an arcuate shape. In various embodiments, the arcuate shape of the first set of members elastically stretches to allow the continuous metal sheet to bend in more than one axis without buckling. In various embodiments, the first set of members and the second set of members define a center cell that contains the corner. In various embodiments, each center cell of the continuous metal sheet has six sides defined by two of the first set of members and two of the second set of members. In various embodiments, the center cell is a concave hexagon. In various embodiments, the first set of members and the second set of members define a unit cell that has a different configuration than the center cell. In various embodiments, the unit cell is a rhomboid. In various embodiments, the unit cell is a rhombus. In various embodiments, the center axis is an axis of symmetry for the first set of members and the second set of members.

While the present disclosure has been shown and described in detail above, it will be clear to the person skilled in the art that changes and modifications may be made without departing from the spirit and scope of the disclosure. For example, the continuous metal sheet having the one or more fenestration patterns could be used alone without the polymer layer in a variety of biomaterial and non-biomaterial applications. As such, that which is set forth in the foregoing description and accompanying drawings is offered by way of illustration only and not as a limitation. The actual scope of the disclosure is intended to be defined by the following claims, along with the full range of equivalents to which such claims are entitled. In addition, one of ordinary skill in the art will appreciate upon reading and understanding this disclosure that other variations for the disclosure described herein can be included within the scope of the present disclosure.

In the foregoing Detailed Description, various features are grouped together in several embodiments for the purpose of streamlining the disclosure. This method of disclosure is not to be interpreted as reflecting an intention that the embodiments of the disclosure require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. A valve, comprising:
    a first frame member having a distal end defining a distal cross-sectional area and a proximal end defining a proximal cross-sectional area larger than the distal cross-sectional area;
    a second frame member having a distal end connected to the proximal end of the first frame member, where the distal end of the second frame member and the proximal end of the first frame member define a circular proximal cross sectional area;
    a third frame member connected to a middle portion of the first frame member, where a proximal end of the third frame member defines a circular proximal cross-sectional area approximately equal to the circular proximal cross-sectional area defined by the distal end of the second frame member and the proximal end of the first frame member;
    a first valve leaflet connected only to the first frame member, the first valve leaflet including a first inflow surface and a first outflow surface opposite the first inflow surface, and being configured to shift between an open position and a closed position; and
    a sinus defined by a volume between the first outflow surface of the first valve leaflet in the open position and the circular proximal cross-sectional area defined by the distal end of the second frame member and the proximal end of the first frame member.

2. The valve of claim 1, including a second valve leaflet connected only to the first frame member opposite the first valve leaflet.

3. The valve of claim 1, including a second valve leaflet and a third valve leaflet connected to the first frame member.

4. The valve of claim 1, including a fourth frame member defining a fourth circular cross-sectional area connected to the distal end of the first frame member.

5. The valve of claim 4, where the fourth circular cross-sectional area is approximately equal to the proximal cross-sectional area of the first frame member.

* * * * *